US012597487B2

(12) United States Patent
Marshall et al.

(10) Patent No.: US 12,597,487 B2
(45) Date of Patent: Apr. 7, 2026

(54) SYSTEMS AND METHODS FOR IDENTIFYING PEPTIDES BY SAMPLING AND FILTERING

(71) Applicant: YYZ Pharmatech Inc., Toronto (CA)

(72) Inventors: John G. Marshall, Toronto (CA); Peter Bowden, Scarborough (CA); Jaimie Dufresne, Orleans (CA)

(73) Assignee: YYZ Pharmatech Inc., Toronto (CA)

( * ) Notice: Subject to any disclaimer, the term of this patent is extended or adjusted under 35 U.S.C. 154(b) by 0 days.

(21) Appl. No.: 18/874,453

(22) PCT Filed: Jun. 30, 2023

(86) PCT No.: PCT/CA2023/050900
§ 371 (c)(1),
(2) Date: Dec. 12, 2024

(87) PCT Pub. No.: WO2024/000077
PCT Pub. Date: Jan. 4, 2024

(65) Prior Publication Data
US 2025/0166735 A1 May 22, 2025

Related U.S. Application Data

(60) Provisional application No. 63/402,157, filed on Aug. 30, 2022, provisional application No. 63/357,534, filed on Jun. 30, 2022.

(51) Int. Cl.
*G16B 30/20* (2019.01)
*G16B 35/20* (2019.01)
*G16B 40/10* (2019.01)

(52) U.S. Cl.
CPC ............. *G16B 30/20* (2019.02); *G16B 35/20* (2019.02); *G16B 40/10* (2019.02)

(58) Field of Classification Search
CPC ............................ G16B 40/10; G01N 2570/00
See application file for complete search history.

(56) References Cited

U.S. PATENT DOCUMENTS

| | | | | |
|---|---|---|---|---|
| 5,538,897 A | * | 7/1996 | Yates, III | G01N 33/6848 530/335 |
| 6,017,693 A | * | 1/2000 | Yates, III | G16B 99/00 435/5 |

(Continued)

FOREIGN PATENT DOCUMENTS

| | | |
|---|---|---|
| CN | 103810200 A | 5/2014 |
| CN | 110277136 A | 9/2019 |

(Continued)

OTHER PUBLICATIONS

Zhu, Peihong, et al. "Peptide-to-protein distribution versus a competition for significance to estimate error rate in blood protein identification." Analytical biochemistry 411.2 (2011): 241-253. (Year: 2011).*

(Continued)

*Primary Examiner* — Jesse P Frumkin
(74) *Attorney, Agent, or Firm* — Mintz, Levin, Cohn, Ferris, Glovsky and Popeo, P.C.

(57) ABSTRACT

Systems and methods for identifying a peptide for a query spectrum. The methods can involve receiving one or more parameters of a query spectrum; generating one or more candidate peptide sequences based on the one or more parameters of the query spectrum; generating a plurality of samples of the query spectrum; selecting at least one sample from the plurality of samples for comparison with the one or more candidate peptide sequences; determining a likelihood indicator for each of the one or more candidate peptide sequences based on a comparison with the at least one sample; applying a signal to noise filter to the one or more candidate peptide sequences based on the likelihood indi- (Continued)

cators for the candidate peptide sequences; and selecting at least one candidate peptide sequence as a proposed peptide sequence for the query spectrum based on the filtered candidate peptide sequences.

32 Claims, 19 Drawing Sheets

Specification includes a Sequence Listing.

(56)                  References Cited

U.S. PATENT DOCUMENTS

| | | | | |
|---|---|---|---|---|
| 6,489,608 | B1 * | 12/2002 | Skilling | H01J 49/04 |
| | | | | 250/281 |
| 6,891,154 | B2 | 5/2005 | Zhu et al. | |
| 11,309,061 | B1 * | 4/2022 | Haseeb | G16B 40/10 |
| 11,798,654 | B1 * | 10/2023 | Kumar | G16B 40/10 |
| 2003/0036207 | A1 * | 2/2003 | Washburn | G16B 50/30 |
| | | | | 702/19 |
| 2004/0033530 | A1 * | 2/2004 | Awrey | G01N 33/6851 |
| | | | | 435/7.1 |
| 2004/0044481 | A1 * | 3/2004 | Halpern | G16B 50/00 |
| | | | | 702/19 |
| 2006/0121618 | A1 * | 6/2006 | Shilov | G01N 33/6842 |
| | | | | 702/19 |
| 2007/0136007 | A1 * | 6/2007 | Bern | G16C 20/90 |
| | | | | 702/27 |
| 2007/0218505 | A1 * | 9/2007 | Kearney | G01N 33/6848 |
| | | | | 435/7.1 |
| 2015/0039240 | A1 * | 2/2015 | Yoshizawa | G01N 33/6848 |
| | | | | 702/19 |
| 2017/0108509 | A1 * | 4/2017 | Parker | G16B 30/00 |
| 2018/0047553 | A1 * | 2/2018 | Richardson | A61B 1/041 |
| 2019/0018928 | A1 * | 1/2019 | Valkenborg | G16B 40/00 |
| 2021/0241851 | A1 * | 8/2021 | Hruska | G16B 40/20 |
| 2022/0208540 | A1 * | 6/2022 | Behsaz | H01J 49/0036 |
| 2024/0280558 | A1 * | 8/2024 | Platt | G01N 33/48792 |

FOREIGN PATENT DOCUMENTS

| | | | | |
|---|---|---|---|---|
| EP | 3739589 | A1 | 11/2019 | |
| WO | WO-2017088769 | A1 * | 6/2017 | G16B 40/10 |
| WO | WO-2020260419 | A1 * | 12/2020 | G01N 33/6848 |

OTHER PUBLICATIONS

International Search Report and Written Opinion for International Patent Application No. PCT/CA2023/050900, mailed Oct. 24, 2023.

Kim et al., "Spectral Dictionaries", Molecular & Cellular Proteomics 8.1, 2009, The American Society for Biochemistry and Molecular Biology, Inc., http://www.mcponline.org.

Z. Z. Chen et al., "LEDGF is a new growth factor in fetal serum", Ryerson Analytical Biochemistry Laboratory (RABL), Department of Chemistry and Biology, Ryerson University, Aug. 2022, https://www.researchgate.net/publication/362660771.

Z. Z. Chen et al., "Mitochondria and cytochrome components released into the plasma of severe COVID-19 and ICU acute respiratory distress syndrome patients", Clinical Proteomics, 2023, https://doi.org/10.1186/s12014-023-09394-0.

Z. Z. Chen et al., "Extraction of naturally occurring peptides versus the tryptic digestion of proteins from fetal versus adult bovine serum for LC-ESI-MS/MS", Analytical Biochemistry 689, 2024, 115497, https://doi.org/10.1016/ j.ab.2024.115497.

Z. Z. Chen et al., "Trypsin Digestion Conditions of Human Plasma for Observation of Peptides and Proteins from Tandem Mass Spectrometry", ACS omega 9, 40, p. 41343-41354, https://doi.org/10.1021/acsomega.4c03955.

J.Dufresne et al., "Selected Ion Extraction of Peptides with Heavy Isotopes and Hydrogen Loss Reduces the Type II Error in Plasma Proteomics", ACS Omega 2025, 10, p. 281-293, https://doi.org/10.1021/acsomega.4c05624.

Z. Z. Chen et al., "Micro scale chromatography of human plasma proteins for nano LC-ESI-MS/MS", Analytical Biochemistry 697, 2025, 115694, https://doi.org/10.1016/j.ab.2024.115694.

Z. Z. Chen et al., "Comparison of the Human Plasma Peptides from the Fit of Fragmentation Spectra versus Accurate Monoisotopic Precursor Mass", ACS Omega 2025, 10, p. 10796-10811, https://doi.org/10.1021/acsomega.4c06211.

T Thavarajah et al., "Re-evaluation of the 18 non-human protein standards used to create the Empirical Statistical Model for Decoy Library Searching", Analytical Biochemistry 599, 2020, 113680, https://doi.org/10.1016/j.ab.2020.113680.

J.Dufresne et al., "Re-evaluation of the rabbit myosin protein standard used to create the empirical statistical model for decoy library searching", Analytical Biochemistry 560, 2018, p. 39-49, https://doi.org/10.1016/j.ab.2018.08.025.

P. Zhu et al., "Peptide-to-protein distribution versus a competition for significance to estimate error rate in blood protein identification", Analytical biochemistry 411, 2011, p. 241-253, https://doi: 10.1016/j.ab.2010.12.003.

P. Zhu et al., "Chi-square comparison of tryptic peptide-to-protein distributions of tandem mass spectrometry from blood with those of random expectation", Analytical biochemistry 409, 2011, p. 189-194, https://doi: 10.1016/j.ab.2010.10.027.

Chick, et al., "A Mass-tolerant Database Search Identifies a Large Proportion of Unassigned Spectra in Shotgun Proteomics as Modified Peptides", Nature Biotechnology 33(7):743-749 (2015).

Eng, et al., "An Approach to Correlate Tandem Mass Spectral Data of Peptides with Amino Acid Sequences in A Protein Database", Journal of the American Society for Mass Spectrometry 5(11):976-989 (1994).

* cited by examiner

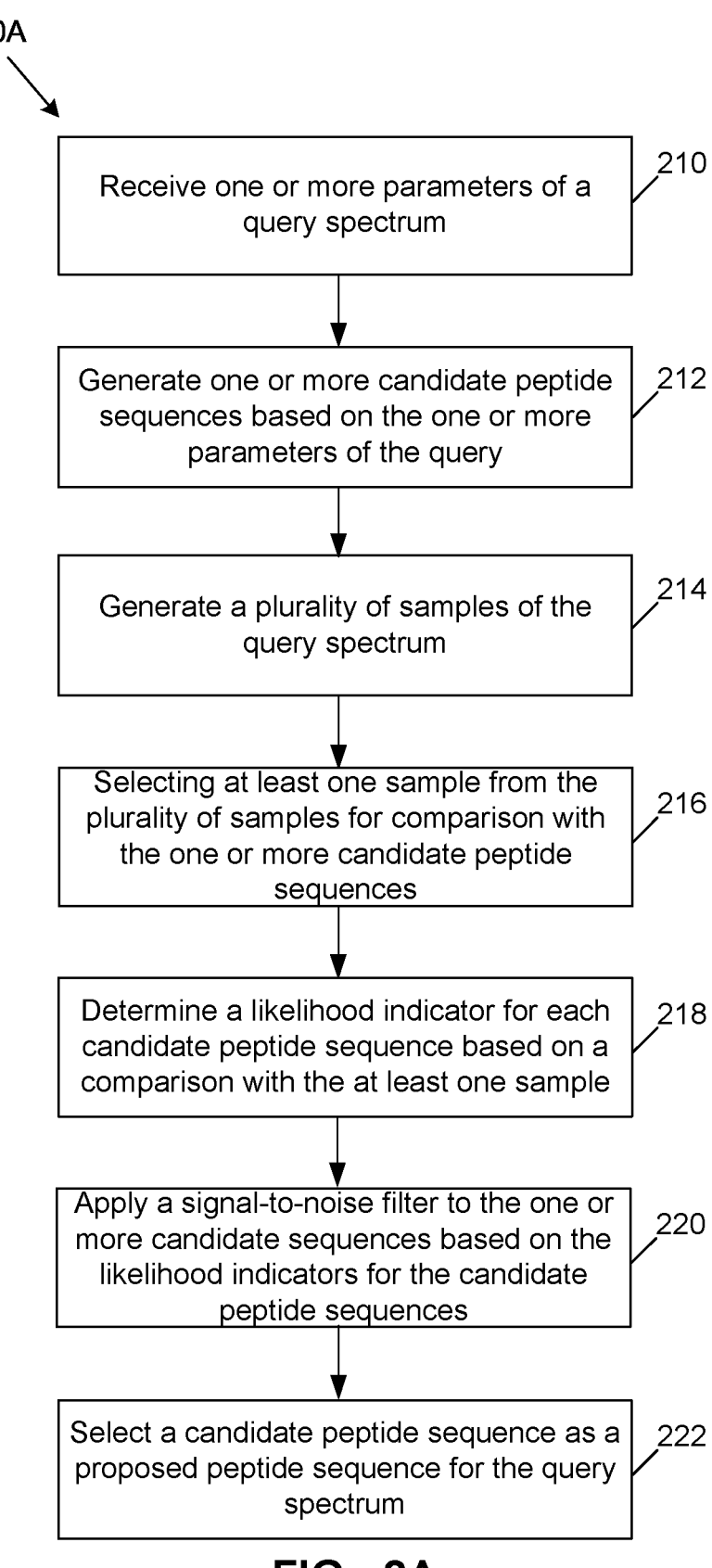

200A

210
Receive one or more parameters of a query spectrum

212
Generate one or more candidate peptide sequences based on the one or more parameters of the query 214
Generate a plurality of samples of the query spectrum 216
Selecting at least one sample from the plurality of samples for comparison with the one or more candidate peptide sequences 218
Determine a likelihood indicator for each candidate peptide sequence based on a comparison with the at least one sample 220
Apply a signal-to-noise filter to the one or more candidate sequences based on the likelihood indicators for the candidate peptide sequences 222
Select a candidate peptide sequence as a proposed peptide sequence for the query spectrum

| Amino Acid Group Code | Group Name | Number of AAs in the Group | AAs |
|---|---|---|---|
| 1 | Anchor for Tryptic Peptide | | Arginine or Lysine |
| 2 | Acidic | | Aspartic Acid or Glutamic Acid |
| 3 | Basic | | Arginine, Histidine or Lysine |
| 4 | Polar Uncharged | | Serine or Threonine |
| 5 | Polar uncharged with amine side chain | | Asparagine or Glutamine |
| 6 | Sulfide R group | | Cysteine or Methionine |
| 7 | Neutral | | Alanine or Valine or Isoleucine or Leucine |
| 8 | Aliphatic | | Phenylalanine or Tyrosine or Tryptophan |
| 9 | Proline | | Proline |

| Peptide length | Combinations without groups | Formula | Number of Combinations With groups |
|---|---|---|---|
| 9 | $20^9 = 5.12 \times 10^{11}$ | 2 * 2 * 3 * 2 * 2 * 2 * 4 * 3 * 1 | 1,152 |
| 10 | $20^{10} = 1.024 \times 10^{13}$ | 2 * 2 * 3 * 2 * 2 * 2 * 4 * 3 * 1 * $20^1$ | 23,040 |
| 11 | $20^{11} = 2.048 \times 10^{14}$ | 2 * 2 * 3 * 2 * 2 * 2 * 4 * 3 * 1 * $20^2$ | 460,800 |
| 12 | $20^{12} = 4.096 \times 10^{15}$ | 2 * 2 * 3 * 2 * 2 * 2 * 4 * 3 * 1 * $20^3$ | 9,216,000 |
| 13 | $20^{13} = 8.192 \times 10^{16}$ | 2 * 2 * 3 * 2 * 2 * 2 * 4 * 3 * 1 * $20^4$ | 184,320,000 |
| 14 | $20^{14} = 5.12 \times 10^{11}$ | 2 * 2 * 3 * 2 * 2 * 2 * 4 * 3 * 1 * $20^5$ | 3,686,400,000 |
| 15 | $20^{15} = 5.12 \times 10^{11}$ | 2 * 2 * 3 * 2 * 2 * 2 * 4 * 3 * 1 * $20^6$ | 7.37287 x $10^{10}$ |
| 16 | $20^{16} = 5.12 \times 10^{11}$ | 2 * 2 * 3 * 2 * 2 * 2 * 4 * 3 * 1 * $20^7$ | 1.47456 x $10^{12}$ |
| 17 | $20^{17} = 5.12 \times 10^{11}$ | 2 * 2 * 3 * 2 * 2 * 2 * 4 * 3 * 1 * $20^8$ | 2.94912 x $10^{13}$ |
| 18 | $20^{18} = 5.12 \times 10^{11}$ | 2 * 2 * 3 * 2 * 2 * 2 * 4 * 3 * 1 * $20^9$ | 5.89824 x $10^{14}$ |
| 19 | $20^{19} = 5.12 \times 10^{11}$ | 2 * 2 * 3 * 2 * 2 * 2 * 4 * 3 * 1 * $20^{10}$ | 1.179648 x $10^{16}$ |

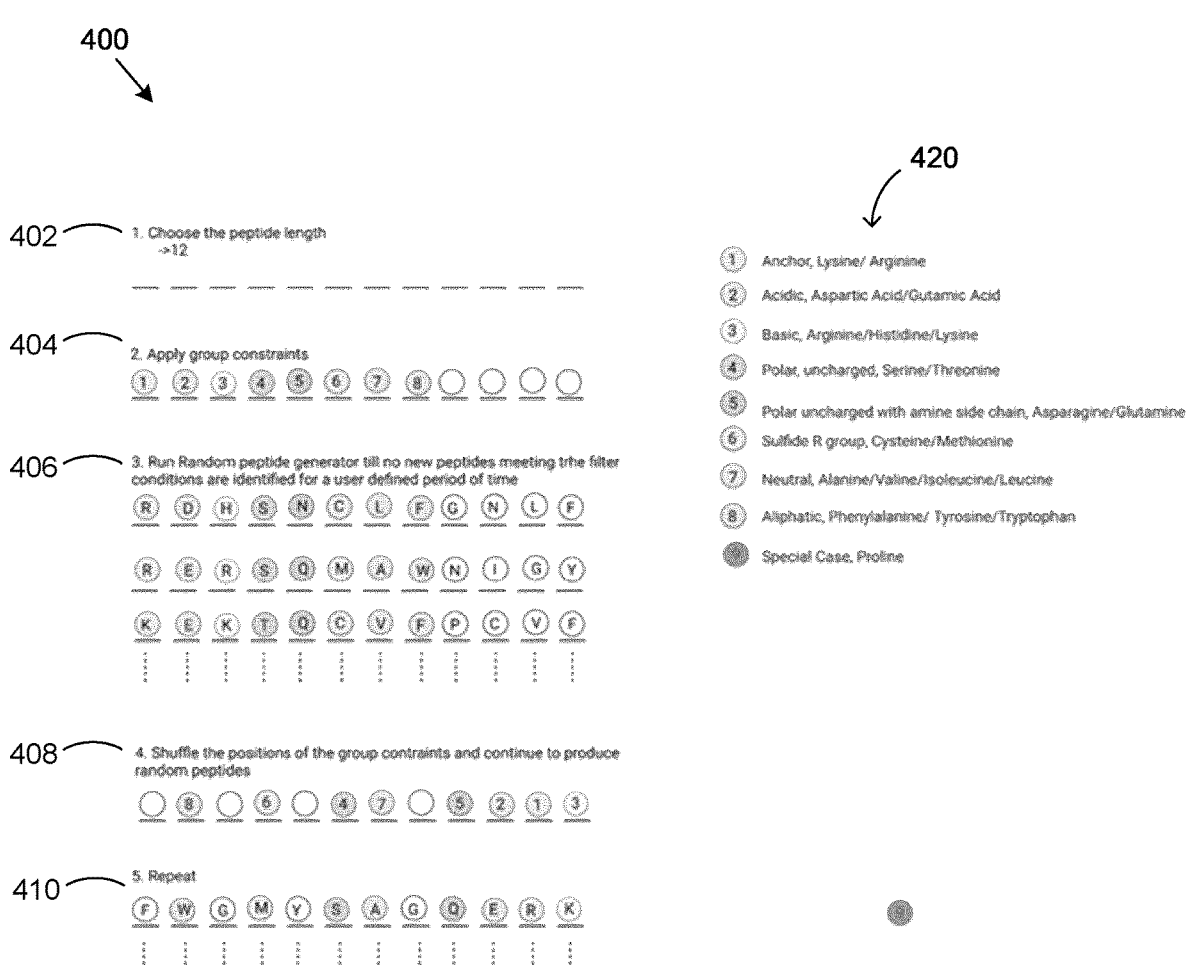

402　1. Choose the peptide length
　　　->12

404　2. Apply group constraints 406　3. Run Random peptide generator till no new peptides meeting trhe filter
　　　conditions are identified for a user defined period of time 408　4. Shuffle the positions of the group constraints and continue to produce
　　　random peptides 410　5. Repeat ① Anchor, Lysine/ Arginine ② Acidic, Aspartic Acid/Gutamic Acid ③ Basic, Arginine/Histidine/Lysine ④ Polar, uncharged, Serine/Threonine ⑤ Polar uncharged with amine side chain, Asparagine/Glutamine ⑥ Sulfide R group, Cysteine/Methionine ⑦ Neutral, Alanine/Valine/Isoleucine/Leucine ⑧ Aliphatic, Phenylalanine/ Tyrosine/Tryptophan ● Special Case, Proline

Figure 4B:
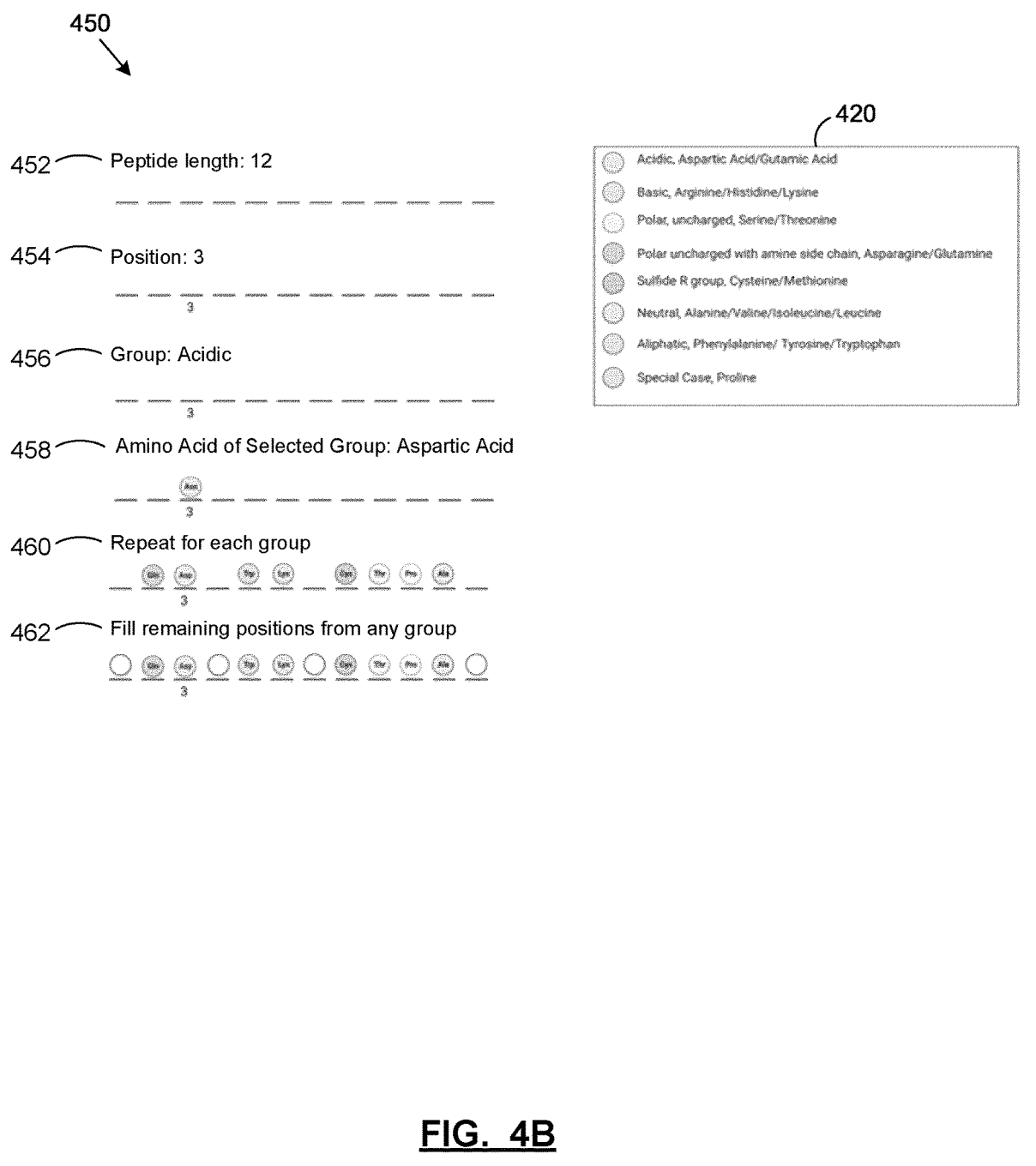

452 ⌒ Peptide length: 12

454 ⌒ Position: 3

3

456 ⌒ Group: Acidic

3

458 ⌒ Amino Acid of Selected Group: Aspartic Acid

3

460 ⌒ Repeat for each group

3

462 ⌒ Fill remaining positions from any group

3

Acidic, Aspartic Acid/Glutamic Acid

Basic, Arginine/Histidine/Lysine

Polar, uncharged, Serine/Threonine

Polar uncharged with amine side chain, Asparagine/Glutamine

Sulfide R group, Cysteine/Methionine

Neutral, Alanine/Valine/Isoleucine/Leucine

Aliphatic, Phenylalanine/ Tyrosine/Tryptophan

Special Case, Proline

| SpectralD | Chi Square | Ion Match Intensity Ratio | Linear Regression F Value | XCorr | Peptide Match Score | Sequential Y Ions | Sequential B Ions | Peptide Sequence |
|---|---|---|---|---|---|---|---|---|
| 1274636 | 0.678426540204911 | 39.1445684523008 | 6711077.6310744 | 0.264932500462487 | 0.5 | 4 | 5 | drVYlHpf |
| 1274636 | 0.502464921635405 | 32.6981832565151 | 60199696.6878402 | 0.06565259 | 0.375 | 4 | 4 | dryVHPif |
| 1274742 | 0.153929907063351 | 15.2654317526695 | 57217363.2115966 | 0.2562451 | 0.375 | 2 | 2 | drpHIFyv |
| 1274664 | 0.162366306156436 | 53.3336027740655 | 56724254.6317708 | 0.08725846 | 0.375 | 2 | 2 | dvyHIRpf |
| 1274780 | 0.616410042553192 | 9.83266086759398 | 56602354.6087256 | 0.09629432 | 0.5 | 4 | 4 | drVYlHpf |
| 1274790 | 0.616410042553192 | 11.8874806780086 | 54821858.2457493 | 0.04553201 | 0.5 | 4 | 5 | drVYlHpf |
| 1274636 | 0.410827405966814 | 31.3410345626478 | 54629987.8307717 | 0.05398199 | 0.375 | 4 | 4 | ivhYDFrp |
| 1274636 | 0.359908173202324 | 34.2674507311732 | 53889503.2247819 | 0.1903703 | 0.375 | 2 | 4 | fhiDYVrp |
| 1274636 | 0.502464921635405 | 30.9290307658501 | 53853559.6076332 | 0.100627 | 0.5 | 2 | 1 | drlYPVnf |
| 1274813 | 0.665052390016761 | 10.0780786989391 | 53280545.2229736 | 0.03975045 | 0.5 | 5 | 5 | drVYlHpf |

| SpectralD | Chi Square | Ion Match Intensity Ratio | Linear Regression F Value | XCorr | Peptide Match Score | Sequential Y Ions | Sequential B Ions | PeptideSequence |
|---|---|---|---|---|---|---|---|---|
| 1270476 | 1.78529099968929 | 29.2394128662216 | 211271061.728369 | 0.04237928 | 0.5 | 11 | 6 | egvnDNEEGFFsar |
| 1270599 | 1.59794029329715 | 32.1364033677353 | 210678465.656152 | 0.03280836 | 0.5 | 11 | 8 | egvnDNEEGFFsar |
| 1270474 | 1.58464505068621 | 20.1791722804833 | 204681788.838737 | 0.06566818 | 0.5 | 12 | 8 | egvnDNEEGFFsar |
| 1270674 | 1.59794029329715 | 30.2493727592326 | 1746265862.898402 | -0.03888801 | 0.5 | 13 | 5 | egvnDNEEGFFsar |
| 1270585 | 0.971745557143989 | 14.7709341696263 | 171662393.233741 | 0.0325199 | 0.5 | 12 | 7 | egvnDNEEGFFsar |
| 1270654 | 0.924733966028441 | 16.5825755330712 | 166152378.7416 | -0.009619764 | 0.5 | 8 | 5 | egvnDNEEGFFsar |
| 1270543 | 1.12228454069704 | 16.0490100327721 | 161686280.33895 | 0.05380786 | 0.5 | 9 | 9 | egvnDNEEGFFsar |
| 1270594 | 1.40640477058351 | 15.9534648010201 | 160503413.02909 | -0.02458429 | 0.5 | 10 | 8 | egvnDNEEGFFsar |
| 1270576 | 1.73483516967551 | 16.3480152275595 | 159152222.320892 | -0.00294040421 | 0.5 | 11 | 9 | egvnDNEEGFFsar |
| 1270519 | 1.33222751869272 | 15.8608341258177 | 150837227.127966 | 0.07780029 | 0.5 | 9 | 6 | egvnDNEEGFFsar |

| Peptide | Charge | ABS Avg Delta Mass | AVG Peptide Match | AVG Intensity Ratio | ID Count |
|---|---|---|---|---|---|
| EGVNDNEEGFFSAR | 2 | 0.1503 | 0.4554 | 0.3451 | 149 |
| EYGLPAVVGVEHATK | 2 | 0.1122 | 0.1333 | 0.1901 | 83 |
| EGVNDNEEGFFSAR | 1 | 0.2345 | 0.2199 | 1.2717 | 76 |
| TLYYAR | 1 | 0.0089 | 0.3333 | 0.1490 | 76 |
| GAIVAIMTQPSANDGK | 2 | 0.4824 | 0.2442 | 0.1235 | 75 |
| ADVQGSVEALAAALQK | 2 | 0.4988 | 0.2297 | 0.1237 | 74 |
| ADISIPIMVGGAALSR | 2 | 0.4906 | 0.1250 | 0.1227 | 74 |
| ADISIPIMVGGAALSR | 2 | 0.4906 | 0.1250 | 0.1227 | 74 |
| ALQIVSR | 1 | 0.0599 | 0.1429 | 0.1333 | 73 |
| GAPAIMKPFEEILR | 2 | 0.0122 | 0.1429 | 0.1350 | 72 |

800
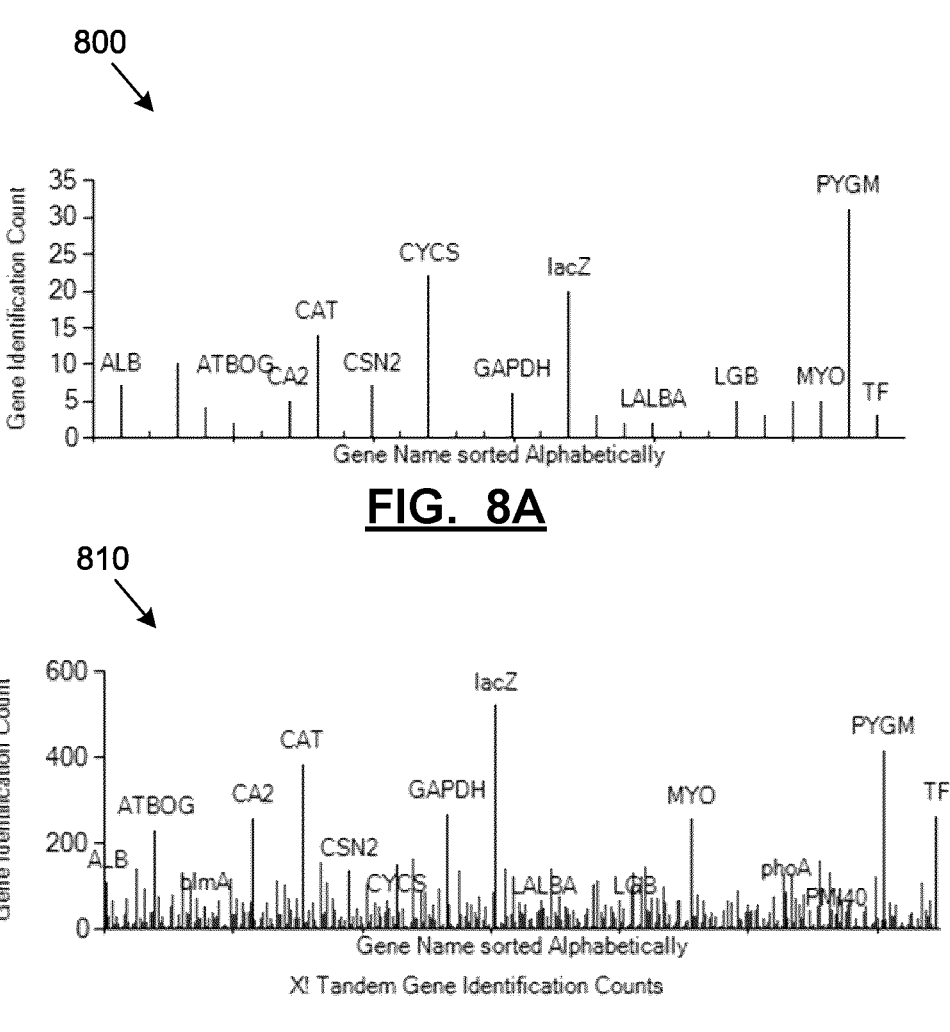
FIG. 8A
810
FIG. 8B
820
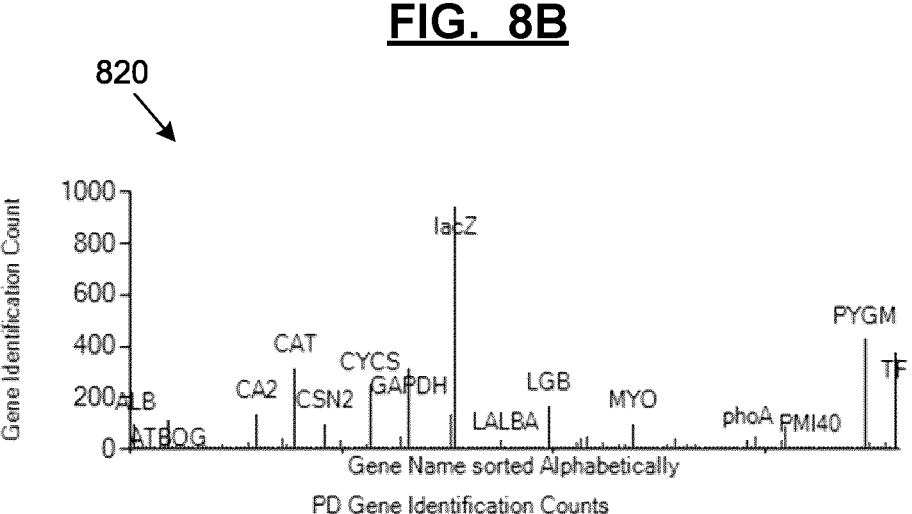
FIG. 8C

1000

Peptide Aptamer            Xtandem

38

6459          1

425

18248          1

123

Sequest

1010

Sequest            Peptide Aptamer

10080

31          47          14514

Xtandem

1020

Sequest            Peptide Aptamer

1826

6          1          21703

Xtandem

1100

1110

1120

1130

1140

1160

| r.squared | adj.r.squared | sigma | Statistic | p.value | df | logLik | AIC | BIC | deviance | df.residual | nobs |
|---|---|---|---|---|---|---|---|---|---|---|---|
| 0.99999939 | 0.99999938 | 0.24266028 | 104743619 | 1.415E-200 | 1 | 0.82764966 | 4.34470069 | 10.9136649 | 3.76857665 | 64 | 66 |
| 0.99999914 | 0.99999911 | 0.25570421 | 325154751 | 1.8426E-86 | 1 | -0.62124465 | 7.2424893 | 11.4460814 | 1.83076997 | 28 | 30 |
| 0.99999861 | 0.99999857 | 0.289657 | 30172839.3 | 1.271E-124 | 1 | -6.89131188 | 19.7826238 | 25.1351927 | 3.52384956 | 42 | 44 |
| 0.99999824 | 0.99999819 | 0.30603937 | 18782900 | 1.5058E-96 | 1 | -7.1916864 | 20.3833728 | 25.049417 | 3.09078314 | 33 | 35 |
| 0.99999867 | 0.99999864 | 0.28711325 | 33012572 | 6.649E-131 | 1 | -6.84636847 | 19.6927369 | 25.1786611 | 3.62709671 | 44 | 46 |

| GeneSymbol | BFPS Count by Linear Regression (Fvalue) | GeneSymbol | BFPS by Chi-squared (JM_X2) | GeneSymbol | BFPS by Xcorr (lag0-mean of 500 lags) |
|---|---|---|---|---|---|
| GluFib | 300 | CD38 | 336 | GluFib | 194 |
| FGL1 | 139 | GluFib | 287 | CCDC9 | 140 |
| CLUH | 100 | FGL1 | 85 | CLUH | 72 |
| CAST | 82 | CAST | 69 | MYH10 | 63 |
| KMT2D | 60 | NDN | 59 | MAPK8IP3 | 61 |
| ADSL | 58 | KMT2D | 48 | KMT2D | 51 |
| CCDC9 | 49 | GPX4 | 28 | GPX4 | 42 |
| IFT81 | 48 | MYH10 | 28 | IFT81 | 27 |
| NDN | 41 | IFT81 | 26 | TIMELESS | 26 |
| MYH10 | 36 | TLR5 | 26 | ADSL | 21 |
| CD38 | 34 | CCDC9 | 21 | PHRF1 | 21 |
| GPX4 | 25 | ACTN2 | 16 | NAV3 | 20 |
| TIMELESS | 23 | MAPK8IP3 | 12 | PGM2 | 20 |
| MAPK8IP3 | 21 | NAV3 | 12 | FGL1 | 16 |
| TLR5 | 19 | ADSL | 10 | RGS7 | 15 |

1220

| GeneSymbol | BFPS Count by Linear Regression (Fvalue) | GeneSymbol | BFPS by Chi-squared (JM_X2) | GeneSymbol | BFPS by Xcorr (lag0-mean of 500 lags) |
|---|---|---|---|---|---|
| SLC35F5 | 155 | C2 | 956 | Bv2 | 200 |
| THRA | 154 | THRA | 187 | TKT | 148 |
| IFT122 | 140 | DNAH9 | 151 | C2 | 88 |
| Bv2 | 126 | Bv2 | 149 | TBC1D14 | 68 |
| DNAH9 | 126 | IFT122 | 82 | HDAC2 | 63 |
| MICAL2 | 98 | TKT | 70 | DNAH9 | 60 |
| CDCA2 | 96 | MICAL2 | 64 | MICAL2 | 57 |
| AngioII | 96 | AngioII | 62 | PSMD11 | 57 |
| C2 | 81 | BEB3 | 59 | MSH4 | 54 |
| TBC1D14 | 74 | TBC1D14 | 56 | IFT122 | 52 |
| HDAC2 | 72 | PSMD11 | 51 | TNS4 | 51 |
| TKT | 61 | SAE1 | 49 | THRA | 50 |
| MSH4 | 56 | MSH4 | 48 | SLC35F5 | 36 |
| PSMD11 | 54 | HDAC2 | 32 | AngioII | 33 |
| STAMBP | 50 | CDCA2 | 31 | MGC148692 | 29 |

SYSTEMS AND METHODS FOR IDENTIFYING PEPTIDES BY SAMPLING AND FILTERING

CROSS-REFERENCE TO RELATED APPLICATIONS

This application is a national stage entry of International Patent Application No. PCT/CA2023/050900, filed Jun. 30, 2023, which claims the benefit of and priority to U.S. Provisional Application No. 63/357,534, filed Jun. 30, 2022, and U.S. Provisional Application No. 63/402,157, filed Aug. 30, 2022, the contents of which are hereby incorporated by reference herein in their entireties.

SEQUENCE LISTING

This application incorporates by reference in its entirety the Sequence Listing XML file entitled "046742.00001.xml" (25 KB), which was created on Dec. 12, 2024, and filed electronically herewith.

FIELD

The described embodiments relate to systems and methods for mass spectrometry. In some example embodiments, the system and methods can relate to identifying peptides.

BACKGROUND

Biological drugs like antibodies or nanobodies are now the most rapidly growing area in drug development. However, while antibodies are large proteins, only the hyper variable binding sites of the antibodies recognize and bind to drug targets, receptors or ligands. Creating monoclonal antibodies, or single chain antibodies, or binding site alone nanobodies is a complex problem that requires cloning and expression of the antibody variable domains that are synthesized and secreted from cells or expressed on the surface of viral phage, which is expensive and time consuming.

Peptide drugs are of enormous health and economic value. Globally, many peptide drugs are in use, in clinical development, or in preclinical studies. Several peptide drugs have received U.S. Food and Drug Administration (FDA) approval in recent years and the proportion of peptide drugs amongst all FDA approved drugs is expected to continue to increase due to breakthroughs in the field of peptide synthesis, peptide drug stabilization and delivery. Producing an efficient method to identify peptide drugs, that is, peptide aptamers would be of enormous benefit to mankind, however, it is an exceptional challenge due to the difficulties of reliably isolating and characterizing peptide aptamers that bind drug targets.

SUMMARY

The various embodiments described herein generally relate to computer-implemented methods (and associated systems configured to implement the methods) of identifying a peptide for a query spectrum.

An example computer-implemented method can involve receiving one or more parameters of a query spectrum; generating one or more candidate peptide sequences based on the one or more parameters of the query spectrum; generating a plurality of samples of the query spectrum; selecting at least one sample from the plurality of samples for comparison with the one or more candidate peptide sequences; determining a likelihood indicator for each of the one or more candidate peptide sequences based on a comparison with the at least one sample; applying a signal to noise filter to the one or more candidate peptide sequences based on the likelihood indicators for the candidate peptide sequences; and selecting at least one candidate peptide sequence as a proposed peptide sequence for the query spectrum based on the filtered candidate peptide sequences.

In some embodiments, selecting at least one sample from the plurality of samples for comparison with the one or more candidate peptide sequences can involve, for each sample: counting a number of matching sequential b and y spectra lines of that sample; and if the number of matching sequential b and y spectra lines of that sample is less than a pre-determined minimum number of spectra lines, excluding that sample from comparison with the one or more candidate peptide sequences.

In some embodiments, selecting at least one sample from the plurality of samples for comparison with the one or more candidate peptide sequences can involve, for each sample: determining a spectra intensity of that sample; determine a number of matching b and y spectra lines; for the matching b and y spectra lines, determining a corresponding sum of the spectra intensity; determining a total sum of the spectra intensity; determining a ratio of the sum of the spectra intensity for the matching b and y spectra lines and the total sum of the spectra intensity; and if the ratio is less than a pre-determined threshold, excluding that sample from comparison with the one or more candidate peptide sequences.

In some embodiments, selecting at least one sample from the plurality of samples for comparison with the one or more candidate peptide sequences can involve, for each sample: determining a precursor mass for that sample; and if the precursor mass is substantially equal to a mass of a candidate peptide sequence, selecting that sample for comparison with the one or more candidate peptide sequences.

In some embodiments, the precursor mass can include at least one of a precursor mass at a charge state of 1, 2, or 3.

In some embodiments, the precursor mass can include a mass shift from one or more post-translational modifications.

In some embodiments, selecting at least one sample from the plurality of samples for comparison with the one or more candidate peptide sequences can involve, for each sample: determining a mass of a theoretical ion of the sample; and if the mass of the theoretical ion is substantially equal to a mass of a base peak, selecting that sample for comparison with the one or more candidate peptide sequences.

In some embodiments, determining a likelihood indicator for each of the one or more candidate peptide sequences based on a comparison with the at least one sample can involve using one or more of linear regression, multiple linear regression, nested regression or linear model.

In some embodiments, can involve determining a likelihood indicator for each of the one or more candidate peptide sequences based on a comparison with the at least one sample, can involve for each sample, using a chi square test to compare theoretical ions of that sample with corresponding theoretical ions of the candidate peptide sequence.

In some embodiments, determining a likelihood indicator for each of the one or more candidate peptide sequences based on a comparison with the at least one sample can involve, for each sample, determining a cross correlation score relative to the candidate peptide sequence.

In some embodiments, applying a signal to noise filter to the one or more candidate peptide sequences based on the likelihood indicators for the candidate peptide sequences can involve: generating random source noise spectra at high frequencies; and determining a difference between the random source noise spectra at high frequencies to the one or more candidate peptide sequences. If the difference does not exceeds a pre-determined threshold difference, the method can involve excluding the sample from selection as a proposed peptide sequence for the query spectrum; otherwise the method can involve including that sample for selection as a proposed peptide sequence.

In some embodiments, generating random source noise spectra at high frequencies can involve using a Monte Carlo random simulation.

In some embodiments, selecting at least one candidate peptide sequence as a proposed peptide sequence for the query spectrum can involve selecting a best fit per spectra at the level of one of a peptide, an accession, or a gene symbol.

In some embodiments, generating one or more candidate peptide sequences based on the one or more parameters of the peptide query can involve one or more of: storing a plurality of peptide sequences in a computer-readable medium; selecting, from the computer-readable medium, at least one of the plurality of stored peptide sequences to use as at least one candidate peptide sequence, based on the one or more parameters; and randomly generating at least one candidate peptide sequence, based on the one or more parameters.

In some embodiments, receiving one or more parameters of a query spectrum can involve receiving the one or more parameters from user input at a computing device. The one or more parameters can include one or more of an amino acid, a position of the amino acid, an amino acid group, or a position of the amino acid group.

In some embodiments, receiving one or more parameters of a query spectrum can involve: receiving the query spectrum; and deriving the one or more parameters from the query spectrum. The one or more parameters can include one or more of a neutral loss, a post-translational modification shift, an immonium ion, a subtraction of a B ion, or a subtraction of a Y ion.

In some embodiments, selecting, from the computer-readable medium, at least one of the plurality of stored peptide sequences to use as at least one candidate peptide sequence, based on the one or more parameters can involve: identifying a subset of peptide sequences from the plurality of stored peptide sequences, each peptide sequence satisfying the one or more parameters; and selecting the at least one candidate peptide sequence from the subset of peptide sequences.

In some embodiments, the plurality of stored peptide sequences can include one or more of a naturally occurring peptide sequence and a synthetic peptide sequence.

In some embodiments, randomly generating at least one candidate peptide sequence, based on the one or more parameters can involve: randomly generating a peptide sequence; determining whether the randomly generated peptide sequence satisfies the one or more parameters; and if the randomly generated peptide sequence satisfies the one or more parameters, use the randomly generated peptide sequence as a candidate peptide sequence, otherwise discard the randomly generated peptide sequence.

In some embodiments, each of the at least one randomly generated candidate peptide sequence can have a pre-determined length.

In some embodiments, randomly generating at least one candidate peptide sequence, based on the one or more parameters can involve, for each randomly generated candidate peptide sequence: assigning at least one amino acid to the randomly generated candidate peptide sequence based on the one or more parameters; randomly selecting an unassigned position of the pre-determined length; and for the unassigned position, randomly selecting an amino acid and assigning the amino acid to the unassigned position. The method can also involve, continue randomly assigning amino acids to the randomly generated candidate peptide sequence until each position is assigned.

In some embodiments, randomly selecting an amino acid can involve: randomly selecting an amino acid group from a plurality of amino acid groups, each amino acid group comprising a plurality of amino acids; and randomly selecting the amino acid from the randomly selected amino acid group.

In some embodiments, each randomly generated candidate peptide sequence can involve at least one amino acid from each amino acid group of the plurality of amino acid groups.

In some embodiments, generating a plurality of samples of the query spectrum can involve one or more of generating experimental spectra or generating simulated spectra.

In some embodiments, generating simulated spectra can involve using a Monte Carlo random simulation.

In another broad aspect, a system for identifying a peptide for a query spectrum is disclosed herein. The system can include a non-transitory computer readable medium and a processor. The processor can be operable to: receive one or more parameters of the query spectrum; generate one or more candidate peptide sequences based on the one or more parameters of the query spectrum; generate a plurality of samples of the query spectrum; select at least one sample from the plurality of samples for comparison with the one or more candidate peptide sequences; determine a likelihood indicator for each of the one or more candidate peptide sequences based on a comparison with the at least one sample; apply a signal to noise filter to the one or more candidate peptide sequences based on the likelihood indicators for the candidate peptide sequences; and select at least one candidate peptide sequence as a proposed peptide sequence for the query spectrum based on the filtered candidate peptide sequences.

In some embodiments, the processor can be operable to, for each sample: count a number of matching sequential b and y spectra lines of that sample; and if the number of matching sequential b and y spectra lines of that sample is less than a pre-determined minimum number of spectra lines, exclude that sample from comparison with the one or more candidate peptide sequences.

In some embodiments, the processor can be operable to, for each sample: determine a spectra intensity of that sample; determine a number of matching b and y spectra lines; for the matching b and y spectra lines, determining a corresponding sum of the spectra intensity; determining a total sum of the spectra intensity; determining a ratio of the sum of the spectra intensity for the matching b and y spectra lines and the total sum of the spectra intensity; and if the ratio is less than a pre-determined threshold, exclude that sample from comparison with the one or more candidate peptide sequences.

In some embodiments, the processor can be operable to, for each sample: determine a precursor mass for that sample; and if the precursor mass is substantially equal to a mass of a candidate peptide sequence, select that sample for comparison with the one or more candidate peptide sequences.

In some embodiments, the precursor mass can include at least one of a precursor mass at a charge state of 1, 2, or 3.

In some embodiments, the precursor mass can include a mass shift from one or more post-translational modifications.

In some embodiments, the processor can be operable to, for each sample: determine a mass of a theoretical ion of the sample; and if the mass of the theoretical ion is substantially equal to a mass of a base peak, select that sample for comparison with the one or more candidate peptide sequences.

In some embodiments, the processor can be operable to, for each sample, use one or more of linear regression, multiple linear regression, or nested regression to determine a likelihood indicator for that sample based on a comparison with the one or more candidate peptide sequences.

In some embodiments, the processor can be operable to, for each sample, use a chi square test to compare theoretical ions of that sample with corresponding theoretical ions of the candidate peptide sequence to determine a likelihood indicator for that sample.

In some embodiments, the processor can be operable to, for each sample, determine a cross correlation score relative to the candidate peptide sequence to determine a likelihood indicator for each of the at least one sample based on a comparison with the one or more candidate peptide sequences.

In some embodiments, the processor can be operable to: generate random source noise spectra at high frequencies; and determine a difference between the random source noise spectra at high frequencies to the one or more candidate peptide sequences. If the difference does not exceed a pre-determined threshold difference, the processor can exclude the sample from selection as a proposed peptide sequence for the query spectrum; otherwise the processor can include that sample for selection as a proposed peptide sequence.

In some embodiments, the processor can be operable to use a Monte Carlo random simulation to generate random source noise spectra at high frequencies.

In some embodiments, the processor can be operable to select a best fit per spectra at the level of one of a peptide, an accession, or a gene symbol.

In some embodiments, the processor can be operable to: store a plurality of peptide sequences in a computer-readable medium; select, from the computer-readable medium, at least one of the plurality of stored peptide sequences to use as at least one candidate peptide sequence of the one or more candidate peptide sequences, based on the one or more parameters; and randomly generate at least one candidate peptide sequence of the one or more candidate peptide sequences, based on the one or more parameters.

In some embodiments, the processor can be operable to: receive the one or more parameters from user input at a computing device, the one or more parameters comprise one or more of an amino acid, a position of the amino acid, an amino acid group, or a position of the amino acid group.

In some embodiments, the processor can be operable to: receive the query spectrum; and derive the one or more parameters from the query spectrum. The one or more parameters can include one or more of a neutral loss, a post-translational modification shift, an immonium ion, a subtraction of a B ion, or a subtraction of a Y ion.

In some embodiments, the processor can be operable to: identify a subset of peptide sequences from the plurality of stored peptide sequences, each peptide sequence satisfying the one or more parameters; and select the at least one candidate peptide sequence from the subset of peptide sequences.

In some embodiments, the plurality of stored peptide sequences can include one or more of a naturally occurring peptide sequence and a synthetic peptide sequence.

In some embodiments, the processor can be operable to: randomly generate a peptide sequence; determine whether the randomly generated peptide sequence satisfies the one or more parameters; and if the randomly generated peptide sequence satisfies the one or more parameters, use the randomly generated peptide sequence as a candidate peptide sequence, otherwise discard the randomly generated peptide sequence.

In some embodiments, each of the at least one randomly generated candidate peptide sequence can have a pre-determined length.

In some embodiments, the processor can be operable to: assign at least one amino acid to the randomly generated candidate peptide sequence based on the one or more parameters; randomly select an unassigned position of the pre-determined length; and, for the unassigned position, randomly select an amino acid and assign the amino acid to the unassigned position. The processor can continue to randomly assign amino acids to the randomly generated candidate peptide sequence until each position is assigned.

In some embodiments, the processor can be operable to: randomly select an amino acid group from a plurality of amino acid groups, each amino acid group comprising a plurality of amino acids; and randomly select the amino acid from the randomly selected amino acid group.

In some embodiments, each randomly generated candidate peptide sequence can include at least one amino acid from each amino acid group of the plurality of amino acid group.

In some embodiments, the processor can be operable to generate experimental spectra or simulated spectra.

In some embodiments, the processor can be operable to use a Monte Carlo random simulation to generate simulated spectra.

BRIEF DESCRIPTION OF THE DRAWINGS

Several embodiments will now be described in detail with reference to the drawings, in which:

FIG. 2A is a flowchart of a method for identifying peptides for a query spectrum, in accordance with an example embodiment;

FIG. 3A is a table of amino acid groups, in accordance with an example embodiment;

FIG. 3B is a table of possible combinations for various pre-determined lengths with at least one amino acid from each amino acid group, in accordance with an example embodiment;

FIG. 4A is an illustration of a random generation of a candidate peptide, in accordance with an example embodiment;

FIG. 4B is an illustration of a random generation of a candidate peptide, in accordance with another example embodiment;

FIG. 7A is a table of likelihood indicators for various candidate peptide sequences selected from memory for a given query spectrum, in accordance with an example embodiment, said table comprising the following sequences: DRVYIHPF (SEQ ID NO: 26), DRYVHPIF (SEQ ID NO: 8), DRPHIFYV (SEQ ID NO: 9), DVYHIRPF (SEQ ID NO: 10), IVHYDFRP (SEQ ID NO: 12), FHIDYVRP (SEQ ID NO: 13), and DRIYPVHF (SEQ ID NO: 14);

FIG. 7B is a table of likelihood indicators for various candidate peptide sequences selected from memory for a given query spectrum, in accordance with an example embodiment, said table comprising the sequence EGVND-NEEGF FSAR (SEQ ID NO: 1);

FIG. 8A is an illustration of results of 18 standard proteins test from a peptide generation system, in accordance with an example embodiment;

FIG. 8B is an illustration of results of 18 standard proteins test from an X!Tandem system;

FIG. 8C is an illustration of results of 18 standard proteins test from a Sequest® (Proteome Discoverer) system;

FIG. 11B is a table of the data for the linear regression models of FIG. 11A;

Figure 1:
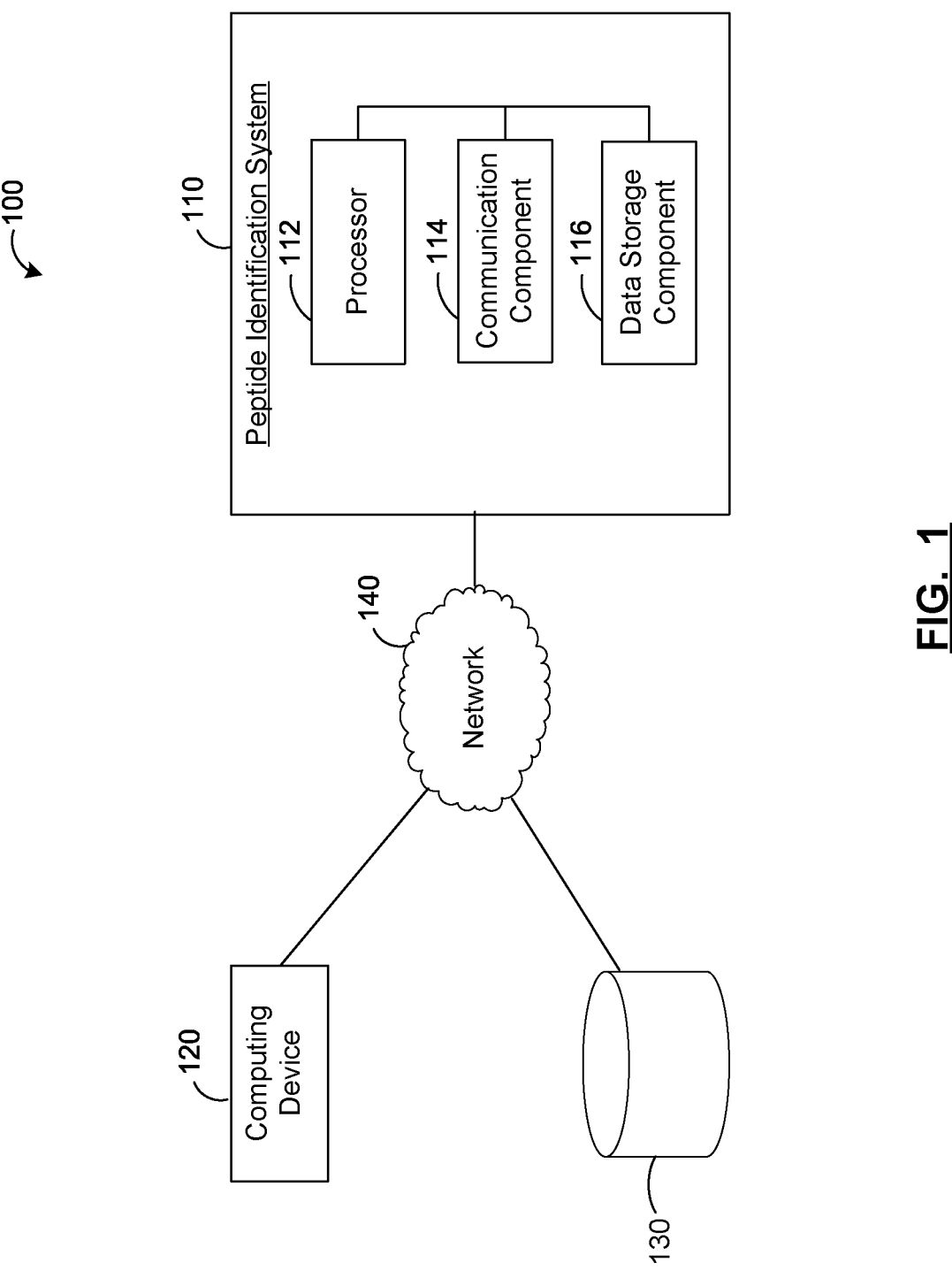
FIG. 1 is a block diagram of components of a peptide identification system, in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

Peptide sequences remain difficult to reliably identify from complex samples by mass spectrometry due to the vast number of possible amino acid and post translational modification combinations.

There are two common strategies for matching spectra to peptides: database searching methods where there is a protein library and de Novo sequence generation methods that do not require a library. The database searching methods, also referred to as library searching, are more common. With the database searching methods, MS/MS spectra are matched to known peptides stored in a database. Database searching requires an in-depth knowledge of the possible peptides in the sample to create a theoretical peptide list and limits the discovery space to known peptides.

In particular, decoy library searching involves searching an existing library that is concatenated with non-existent, i.e., fictious, peptides of similar length and amino acid distributions. However, on average, decoy library searching methods match less than half of all spectra collected. Studies have found that low matching of decoy library searching methods can be attributed in large part to the assignment of MS/MS spectra from actual peptides to non-existent peptides from the concatenated decoy and unaccounted for combinations of post translational modifications. It has been shown that peptides may be fit by MS/MS fragment spectra alone and the peptide mass may be permitted to vary by plus or minus hundreds of Daltons to capture all post translational modifications. A mass-tolerant database search identifies a large proportion of unassigned spectra in shotgun proteomics as modified peptides (Nat Biotechnol. 33:743-9) but the approach is computationally intensive. In this regard, the cost and efficiency of computer searching is rapidly increasing and may require new algorithms to compute false positive rates and new signal to noise filters.

Other studies point to poor matching due to unaccounted for combinations of post translational modifications. Low matching is also a result of the decoy library searching strategy itself. It assumes a lower number of degrees of freedom that there ought to be given the raw data is the spectra and that data is nearly continuous.

The library searching method depends on a well annotated library. Therefore, database searching methods are limited to samples that have sufficiently annotated peptide libraries. Even in well annotated libraries, the peptide corresponding to a particular MS/MS may not be present. The peptide may not be annotated, may be from a different species, or may arise from a genetic mutation. For the purposes of discovery, it would be advantageous to be able to identify drug target binding peptides without a peptide library.

De novo methods aim to identify peptide sequences using a series of rules without the use of a peptide library and are generally computationally expensive.

Conventional de novo sequencing methods aim to identify peptide sequences without the use of a peptide library of possible amino acid sequences and result in a vast search space made even larger by a multitude of possible post translational modifications. De novo methods may be biased and there is a need for a probability-based mechanism for selecting the correct sequence from many possible de novo amino acid sequences. The probability-based mechanism may involve computing the goodness of fit or correlation or linear model but also may be empirically based on observation frequency with respect to computer random or physical generated random (i.e., noise) MS/MS spectra.

Disclosed herein are systems and methods for identifying peptides from MS/MS spectra where peptides can be retrieved from a known annotated library or generated using a random peptide generator. The random generation of peptides can be performed at run time. Furthermore, a combination of user-imposed constraints and de novo-style rules of thumb can be applied to narrow the possible combinations of peptide sequences. Also disclosed are systems and methods for creating synthetic peptide libraries, in which a peptide length and groups of amino acids are selectable. Such features allow a peptide list with desired characteristics to be created, which can reduce the search space for the random peptide generator. The system and methods can be used to identify peptide drugs and/or aptamers.

A direct method to isolate peptide binding regions from direct interaction with drug target receptors, ligands and diagnostic or prognostic proteins is therefore desirable.

In some embodiments, the methods and systems disclosed herein relate to screening naturally occurring and/or synthetic peptide libraries by direct binding to immobilized drugs, drug targets, ligands, receptors, markers or other proteins or biopolymers or biomolecules or biochemicals or chemical drugs or moieties thereof, hereafter referred to as the "Binding Target using LC-ESI-MS/MS".

The methods and systems disclosed herein can use a real physical library of naturally occurring and/or random synthetic peptides and/or polypeptides. A real, physical library herein refers to a plurality of peptides that can be used experimentally, such as poured over a binding target.

The methods and systems disclosed herein can involve the use of samples prepared according to known methods. For example, samples can be prepared by: (1) immobilizing a binding target on a surface; (2) interacting the immobilized binding target with a natural or synthetic library of polypeptides; (3) washing away unbound polypeptides; and (4) eluting the bound polypeptides, such as by salts or surfactants or acids or base or organic solvents or chaotropes or any combination thereof. The methods and systems further involve analyzing the bound, washed, and eluted polypeptides by LC-ESI-MS/MS or LC-ESI-MSN either directly or after chemical or enzymatic modification. In some embodiments, the MS/MS or MSn can be fit to peptide sequences with or without a database or using statistical methods to fit the peptides to randomly generated or other peptides. Optionally, the methods and systems can also involve using the principles of peptide library design and de novo sequencing to constrain and guide the creation of a peptide library based on the amino acid composition determined from MS, MS/MS, and/or MSn. The methods and systems disclosed herein can further involve: generating the in silico peptide library to match the characteristics of the physical library used in the experiment and reducing the dimension for each MS/MS or MSn spectra searched using the observed amino acids from the MS/MS or MSn spectra; fitting the observed MS/MS or MSn spectra from the physical peptide that bound the target to the possible peptide in the in silico library using de novo, or goodness of fit, or regression or linear models or correlation or heuristic algorithms to determine the amino acid sequence and the molecular composition of matter of the physical peptide that bound the target; and synthesizing and testing the specifically identified peptide for binding to the target molecule to act as a drug, or ligand, or receptor, or diagnostic or prognostic affinity binding reagent. The methods and systems disclosed herein can be iterative where the resulting peptide obtained from a first pass in the process is used to guide modifications to the physical peptides library for a subsequent round of refinement. The systems and methods disclosed herein can be used to create new biological drugs (i.e., peptide aptamers) without the cloning and express steps presently used to create monoclonal antibodies, nanobodies or phage binding site sites.

The methods and systems disclosed herein can involve: cloning and covalently fixing targets to high throughput 96 well pvdf plates or micro/nano surfaces or targets tagged in solution; applying libraries of known or unknown natural or synthetic peptides for binding, washing, eluting (with salt, organic, acid, base, competitor, analog, or labelled compound) and finely separating the sample into discreet fractions by nanospray liquid chromatography (e.g., MALDI, Electrospray or other ionization methods) and MSn fragmentation by gas collision or impact, chemical or electron impact or electrical energy or acceleration or atom collision or interaction with other particles; and using a search engine and proteomics platform that leverages key aspects of spectra library searching and random peptide generators to identify peptide drugs.

The methods and systems disclosed herein can match spectra from a sample to peptide sequences. In some embodiments, the search engine can use a combination of scoring algorithms, for example, based on a spectra line count, a count of sequential ions, and fitting algorithms based on chi square, linear regression, amino acid matching and a signal to noise intensity score to identify peptide sequences. The search engine can toggle back and forth between spectra generated from a reference library and a random number generator given certain parameters depending on the nature of the experiment. The search engine employs a series of nested loops and can map fragments onto their respective precursor masses for multiple levels of fragmentation events (MSn). The disclosed embodiments can validate results by for example, counting a number of spectra in the sample that match each identified peptide sequence and comparing this count with a count for randomly simulated and/or experimentally derived (e.g., blank noise) spectra.

Reference is now made to FIG. 1, which illustrates a block diagram 100 of components interacting with a peptide identification system 110. As shown in FIG. 1, the peptide aptamer identification system 110 is in communication with a computing device 120 and an external data storage 130 via a network 140.

The peptide identification system 110 includes a processor 112, a communication component 114, and a (relational) data storage component 116. The peptide identification system 110 can be provided on one or more computer servers that may be distributed over a wide geographic area and connected via the network 140.

The processor 112, the communication component 114, and the data storage component 116 can be combined into a fewer number of components or can be separated into further components. In some cases, one or more of the components may be distributed over a wide geographic area. The processor 112, the communication component 114, and the data storage component 116 may be implemented in software or hardware, or a combination of software and hardware.

The processor 112 can operate to control the operation of the peptide identification system 110. The processor 112 can initiate and manage the operations of each of the other components within the peptide identification system 110. The processor 112 may be any suitable processors, controllers or digital signal processors, graphics processing unit, application specific integrated circuits (ASICs), and/or field programmable gate arrays (FPGAs) that can provide sufficient processing power depending on the configuration, purposes and requirements of the peptide identification system 110. In some embodiments, the processor 112 can include more than one processor with each processor being configured to perform different dedicated tasks. The processor 112 can execute various instructions stored in the data storage 116 to implement the various methods described herein.

The communication component 114 may include any interface that enables the peptide identification system 110 to communicate with other devices and systems. In some embodiments, the communication component 114 can include at least one of a serial port, a parallel port or a USB port. The communication component 114 may also include an interface to a component via one or more of a Bluetooth®, WiFi, Internet, Local Area Network (LAN), Ethernet, Firewire, modem, fiber, or digital subscriber line connection. Various combinations of these elements may be incorporated within the communication component 114. The communication component 114 can be used to communicate with the computing device 120, for example, to receive a query MS/MS spectrum and one or more parameters for the query MS/MS spectra.

For example, the communication component 114 may receive input from various input devices, such as a mouse, a keyboard, a touch screen, a thumbwheel, a track-pad, a track-ball, a card-reader, voice recognition software and the like depending on the requirements and implementation of the peptide identification system 110.

The data storage component 116 can include RAM, ROM, one or more hard drives, one or more flash drives or some other suitable data storage elements such as disk drives, etc. The data storage component 116 can include one or more databases for storing information relating to peptide sequences, amino acids, and amino acid groups. The data storage 116 can also store data used to perform one or more tests, such as but not limited to precursor tests and base peak tests. The data storage 116 can also store instructions that can be executed by the processor 112 to implement the various methods described herein.

Similar to the data storage component 116, the external data storage 130 can also include RAM, ROM, one or more hard drives, one or more flash drives or some other suitable data storage elements such as disk drives, etc. In some embodiments, the external data storage 130 can be similar to the data storage 116 but located remotely from the peptide identification system 110 and accessible via the network 140. The external data storage 130 can include one or more databases for storing information relating to peptide sequences, amino acids, and amino acid groups. Furthermore, the external data storage 130 can also store data used to perform one or more tests, such as but not limited to precursor tests and base peak tests. The external data storage 130 can store various data associated with the operation of the peptide identification system 110, similar to the data storage 116.

The computing device 120 can include any networked device operable to connect to the network 140. A networked device is a device capable of communicating with other devices through a network such as the network 140. A network device may couple to the network 140 through a wired or wireless connection. Although only one computing device 120 is shown in FIG. 1, it will be understood that more computing devices 120 can connect to the network 140.

The computing device 120 may include at least a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these.

The network 140 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX, Ultra-wideband, Bluetooth®), SS7 signaling network, fixed line, local area network, wide area network, and others, including any combination of these, capable of interfacing with, and enabling communication between, the peptide identification system 110, the computing device 120, and the external data storage 130.

It will be understood that some components of FIG. 1, such as components of the peptide identification system 110 or the external data storage 130, can be implemented in a cloud computing environment.

Figure 2B:
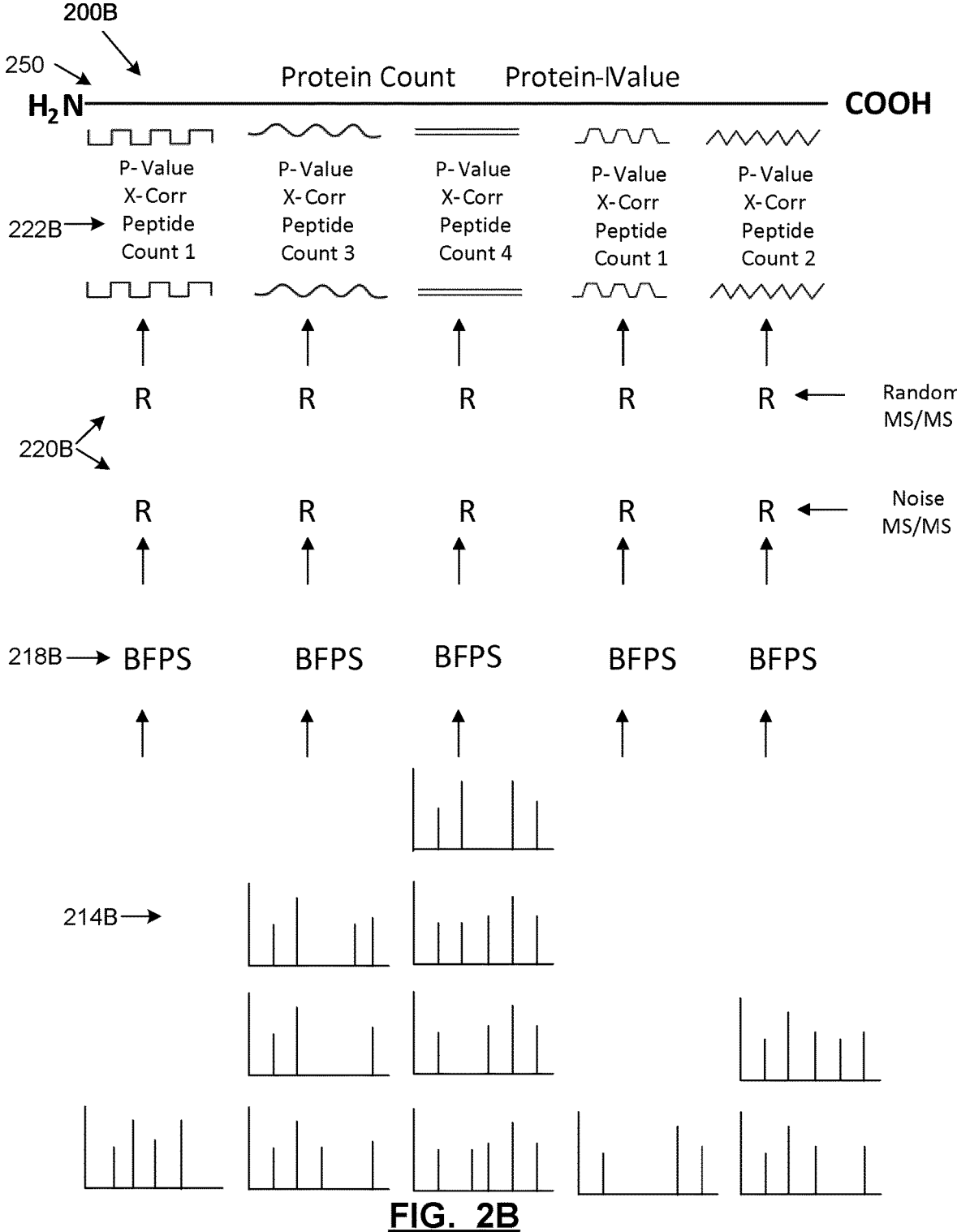
FIG. 2B is a schematic diagram of a method for identifying peptides for a query spectrum, in accordance with an example embodiment.

Reference now is made to FIG. 2A, which illustrates a flowchart for a method 200A for identifying a peptide for a query spectrum, in accordance with some embodiments. Reference is simultaneously made to FIG. 2B, which illustrates a schematic diagram of a method 200B for identifying a peptide for a query spectrum, in accordance with some embodiments. To assist with the description of the method 200A and 200B shown in FIGS. 2A-2B, reference will be made simultaneously to FIGS. 3A to 6B. A peptide identification system, such as peptide identification system 110 having a processor 112 can be configured to implement method 200. The query spectrum can correspond to a sample.

Method 200 can begin at 210, when a processor, such as processor 112 can receive one or more parameters of the query spectrum. The processor 112 can receive the one or more parameters from a computing device, such as computing device 130, via a network, such as network 140.

In some embodiments, the one or more parameters can be received from user input at the computing device 130. For example, the one or more parameters can be one or more of an amino acid or an amino acid group. In addition, a position corresponding to each of the amino acid or the amino acid group can be included.

In some embodiments, the processor 112 can receive the query spectrum and derive the one or more parameters from the query spectrum. For example, the one or more parameters can be one or more of a neutral loss-including ammonia losses and water losses, a post-translational modification shift-which may only be located on a small group of amino acids, an immonium ion (e.g., methionine oxidation), a subtraction of a B ion, or a subtraction of a Y ion.

At 212, the processor 112 can generate one or more candidate peptide sequences based on the one or more parameters. In some embodiments, generating one or more candidate peptide sequences can involve selecting, from the memory, at least one of a plurality of peptide sequences stored in memory to use as at least one candidate peptide sequence. The plurality of peptide sequences can be stored in memory, such as data storage component 130 or data storage component 116. For example, the plurality of peptide sequences can be stored in a peptide database or library. In some embodiments, the plurality of peptide sequences can include naturally occurring peptide sequences and/or synthetic peptide sequences. Selecting candidate peptide sequences from the memory can be suitable when natural aptamers are from a known source and/or where the possible peptide sequences are known (e.g., but not limited to digested plasma).

The selection of candidate peptide sequences from memory can be based on the one or more parameters received at 210 that can be used as constraints to narrow the search space of candidate peptide sequences. For example, the one or more parameters can include a particular amino acid (e.g., lysine or arginine) for the candidate peptide sequence. The processor 112 can identify peptide sequences from the plurality of peptide sequences stored in memory having the particular amino acid and then select the candidate peptide sequences from amongst the peptide sequences having the particular amino acid.

In a further example, the one or more parameters can also include a particular position (e.g., last position) for the particular amino acid. The processor 112 can identify peptide sequences from the plurality of peptide sequences stored in memory having the particular amino acid in the particular position and then select the candidate peptide sequences from amongst the peptide sequences having the particular amino acid in the particular position.

In another example, the one or more parameters can include at least one amino acid group for the candidate peptide sequence (e.g., basic, acidic, neutral, aliphatic or polar amino acid). Each amino acid group can include a plurality of amino acids. Similarly, the processor 112 can identify peptide sequences from the plurality of peptide sequences stored in memory having an amino acid within the amino acid group and then select the candidate peptide sequences from amongst the peptide sequences having an amino acid of the amino acid group.

In some embodiments, the one or more parameters can include both at least one particular amino acid and at least one particular amino acid group. Other constraints are possible.

In yet a further example, the one or more parameters can also include a particular position (e.g., last position) for the amino acid of a particular amino acid group. The processor 112 can identify peptide sequences from the plurality of peptide sequences stored in memory having an amino acid of the particular amino acid group in the particular position and then select the candidate peptide sequences from amongst the peptide sequences having an amino acid in the particular amino acid in the particular position.

In some embodiments, generating a plurality of candidate peptide sequences can involve randomly generating at least one candidate peptide sequence. Randomly generating candidate peptide sequences can be suitable with synthetic peptide sequences or unknown peptide aptamers.

In at least one embodiment, the processor 112 can randomly generate a peptide sequence and determine whether the randomly generated peptide sequence satisfies the one or more parameters. If the randomly generated peptide sequence satisfies the one or more parameters, the processor 112 can use the randomly generated peptide sequence as a candidate peptide sequence. However, the search space can be vast. Instead, the search space for randomly generated sequences can be limited by processing power limitations. In some embodiments, supercomputers or quantum computing can be used to achieve such processing in a timely manner.

In some embodiments, the one or more parameters received at 210 can be used as constraints to narrow the possible combinations for randomly generated candidate peptide sequences. For example, the one or more parameters can include a pre-determined length for the randomly generated candidate peptide sequence. With a pre-determined length of 5, the possible combinations for randomly generated candidate peptide sequences is 3.2 million. Generally, identification of longer peptides involves greater processing power.

Additional constraints can be used to further narrow the possible combinations for randomly generated candidate peptide sequences. The one or more parameters can relate to a minimum number of amino acids from particular amino acids groups, a particular position for an amino acid from the particular amino acid group, a particular amino acid, and a particular position for the particular amino acid, a neutral loss, a post-translational modification shift, an immonium ion, a subtraction of a B ion, or a subtraction of a Y ion.

In some embodiments, the processor 112 can assign at least one amino acid to the randomly generated candidate peptide sequence based on the one or more parameters. For example, the processor 112 can assign a particular amino acid to a particular position, based on the one or more parameters. The processor 112 can then randomly assign amino acids for the remaining unassigned positions.

Reference is now made to FIG. 3A, which illustrates a table 300 for different amino acids groups 302. Amino acid groups can include, for example, an anchor for tryptic peptide, acidic, basic, polar uncharged, polar uncharged with amine side chain, sulfide R, neutral, aliphatic, and proline. Each amino acid group can include any number of amino acids, as indicated by 304. For example, anchor for tryptic peptide can include two amino acids: arginine and lysine, which are indicated by 306. Acidic amino acids can include two amino acids: aspartic acid and glutamic acid. Basic amino acids can include arginine, histidine, and lysine. Polar uncharged amino acids can include serine and threonine. Polar uncharged with amine side chain amino acids can include asparagine and glutamine. Sulfide R amino acids can include cysteine and methionine. Neutral amino acids can include alanine, valine, isoleucine, and leucine. Aliphatic amino acids can include phenylalanine, tyrosine, and tryptophan. Finally, proline amino acids can include proline itself. In some embodiments, the proline amino acids group can be a special case.

In some embodiments, each randomly generated candidate peptide sequence can include at least one amino acid from each amino acid group. That is, the minimum number of amino acids is one for each amino acid group. Requiring each randomly generated candidate peptide sequence to include at least one amino acid from each of the amino acid groups can significantly reduce the possible combinations. FIG. 3B shows a table 320 of the possible combinations for various pre-determined lengths with at least one amino acid from each amino acid group. In some embodiments, a peptide length of 11 or 12 with the requirement of at least one amino acid from each of the amino acid groups can be used.

In some embodiments, randomly generating a candidate peptide sequence for a pre-determined length can involve randomly selecting an unassigned position within the candidate peptide sequence. For the unassigned position, the processor 112 can randomly select an amino acid group from a plurality of amino acid groups and randomly select an amino acid from the selected amino acid group. The selected amino acid can be assigned to the unassigned position and the processor 112 can continue until each position is assigned. That is, the processor 112 can randomly select another unassigned position, randomly select an amino acid group from a plurality of amino acid groups, and randomly select an amino acid from the selected amino acid group to be assigned to the unassigned position.

When the randomly generated candidate peptide sequence requires at least one amino acid from each amino acid group, the subsequent random amino acid group selection can be from amongst the unselected amino acid groups. However, other methods are possible for ensuring that at least one amino acid from each amino acid group is included in the randomly generated candidate peptide sequence.

Reference is now made to FIG. 4A, which illustrates an example random generation 400 of a candidate peptide sequence. As shown at 402, a pre-determined length is used. As shown in FIG. 4A, a pre-determined length of 12 is used. At 404, amino acid group constraints are applied. That is, each group, with the exception of the special case group, is assigned to a position. The special case group has only one amino acid, namely proline. Proline does not fall into any of the other categories.

At 406, for each position having an amino acid group constraint, an amino acid from that amino acid group is randomly selected. For each position without an amino acid group constraint, an amino acid from any amino acid group is randomly selected. The randomly selected amino acids are compared with the filter conditions. If the randomly selected amino acid does not satisfy the filter condition, another amino acid from the group is selected for that position. If the randomly selected amino acid satisfies the filter condition, the amino acid assigned to that position is retained. The peptides that meet the filter conditions continue to be generated until no new peptides are generated or until a user defined amount of time elapses that triggers the position of the constraints to be shuffled and new peptides to be generated.

At 408, the group constraints applied at 404 are shuffled. In some embodiments, shuffling can involve the selection of a different amino acid from the group for that position. In some embodiments, the group constraints may not be shuffled. At 410, amino acids are randomly selected for the unassigned positions. The randomly generated peptides as per the randomized position are in the "peptide template box". A deadman timer switch is running, and is reset each time a novel random peptide is generated. If the time period set in the "infinite loop control" group expires, the peptide template is reshuffled, similar to reshuffling a deck of cards. The random generator restarts using this new peptide template. This process repeats itself indefinitely, hence the term "infinite loop control".

Reference is now made to FIG. 4B, which illustrates another example random generation 450 of a candidate peptide sequence. As shown at 452, a pre-determined length is used. As shown in FIG. 4B, a pre-determined length of 12 is used. At 454, an unassigned position is randomly selected.

As shown in FIG. 4B, all 12 positions are unassigned and position 3 is randomly selected. At 456, an amino acid group from 420 is randomly selected. As shown in FIG. 4B, the acidic amino acid group is randomly selected. At 458, an amino acid from the acidic amino acid group is randomly selected. As shown in FIG. 4B, aspartic acid is randomly selected.

At 460, additional unassigned positions are assigned until the candidate peptide sequence includes at least one amino acid from each of the amino acid groups 420.

At 462, additional unassigned positions are assigned until each position of the candidate peptide sequence is assigned. The randomly selected amino acids assigned at 462 can be from any of the amino acid groups 420.

In some embodiments, candidate peptide sequences can be randomly generated to include known amino acids at known or unknown positions. Furthermore, the randomly generated candidate peptide sequences can be tailored to what is known about a particular binding target.

In some embodiments, the processor 112 can determine whether to select candidate peptide sequences from memory or by randomly generating candidate peptide sequences based on the one or more parameters received from the computing device 120.

In some embodiments, the one or more parameters can include a parameter specified by the user for selecting whether to select candidate peptide sequences from memory or by randomly generating candidate peptide sequences. In some embodiments, the processor 112 can compare the one or more parameters to certain thresholds and determine whether to select candidate peptide sequences from memory or by randomly generating candidate peptide sequences.

In some embodiments, candidate peptide sequences can be selected from memory and randomly generated. For example, a subset of amino acids can be identified from a protein database and then the candidate peptide sequence can be randomly generated to identify post translational modifications (PTM) by including the amino acid masses with mass shifts, depending on the nature of the PTM.

In some embodiments, the peptide identification system 110 can initially select candidate peptide sequences from memory. Depending on the likelihood indicators, the peptide identification system 110 can operate again for the same query spectrum but with candidate peptide sequences randomly generated.

Returning now to FIG. 2, at 214, the processor 112 can generate a plurality of samples of the query spectrum for which a peptide is being identified. In some embodiments, the samples of the query spectrum can be generated experimentally or by simulation. In some embodiments, the simulation can be a Monte Carlo random simulation. Generating a plurality of samples can involve generating spectra lines of the samples as shown at 214B.

At 216, the processor 112 can select at least one sample from the plurality of samples for comparison with the one or more candidate peptide sequences generated at 212. Selecting samples of the plurality of samples for comparison can reduce the computational burden of fitting a large dataset to a large search space. In order to select samples for comparison, one or more signal processing filters can be applied. Signal processing filters can include minimum spectra counting, maximum spectra lines filtering, precursor mass testing, base peak testing, and/or delta mass filtering.

Minimum spectra counting involves discarding spectra with line counts lower than a given threshold as there is likely not enough information below the threshold of spectra lines to make a reliable peptide match. For minimum spectra counting, in some embodiments, the processor 112 can count a number of spectra lines of a sample. In some embodiments, the processor 112 can count the number of matching sequential ion (e.g., b and y ions) spectra lines. If the number of spectra lines of the sample or the number of matching sequential ion spectra lines is less than a pre-determined minimum number of spectra lines, the processor 112 can exclude that sample from comparison with the one or more candidate peptide sequences. In some embodiments, a correction is applied to the number of matching sequential ion spectra lines. For example, a ratio of the number of matching sequential ion spectra lines and the total number of spectra lines can be determined and the pre-determined minimum number of spectra lines can correspond to a pre-determined minimum ratio. In some embodiments, the pre-determined minimum number of spectra lines can be specified by the user. For example, the pre-determined minimum number of spectra lines can be a parameter received from computing device 120.

Maximum spectra lines filtering involves restricting the processor 112 to using the most intense spectra. For maximum spectra lines filtering, the processor 112 can determine a spectra intensity of a sample. In some embodiments, the processor 112 can determine the sum of the spectra intensities of matching ion spectra lines, determine the total sum of the spectra intensity (i.e., the sum of the spectra intensities of all of the spectra lines), determine the ratio of the sum of the spectra intensities of the matching ion spectra lines and the total sum of the spectra intensity. If the ratio is less than a pre-determined threshold, the processor 112 can exclude that sample from comparison with the one or more candidate peptide sequences. In some embodiments, the pre-determined spectra intensity can be based on a candidate peptide sequence, such as a percentage of the spectra intensity of a candidate peptide sequence. The percentage of the spectra intensity can be specified by the user. For example, the percentage of the spectra intensity can be a parameter received from computing device 120. In this manner, with the pre-determined spectra intensity being based on a candidate peptide sequence, the maximum spectra lines filtering can be applied dynamically. The max spectra relates to the intensity values. Assuming a max spectra value of 50 the engine would only examine the 50 most intense spectra lines. This significantly reduces the computation time as a single MS2 spectra can contain thousands of spectra lines.

Precursor mass testing involves comparing a precursor mass of a sample to the mass of a candidate peptide sequence. Samples having a precursor mass matching the mass of any candidate peptide can be further processed. Samples having a precursor mass that does not match any candidate peptide can be discarded from further consideration, and the next sample is assessed.

Precursor mass testing can involve the processor 112 determining a precursor mass for a sample. If the precursor mass is substantially equal to a mass of a candidate peptide sequence of the one or more candidate peptide sequences, the processor 112 can select that sample for comparison with the one or more candidate peptide sequences. The processor 112 can consider the precursor mass to be substantially equal to a mass of a candidate peptide sequence within a pre-determined error range of the mass of the candidate peptide sequence. In some embodiments, the pre-determined error range can be specified by the user. For example, the pre-determined error range can be a parameter received from computing device 120.

In some embodiments, the processor 112 can determine a precursor mass for a sample at different charge states. For example, the processor 112 can determine precursor masses at charge states of 1, 2, and 3.

In some embodiments, the processor 112 can determine a precursor mass for a sample that also considers the presence of one or more post-translational modifications (PTMs). For example, the precursor mass can include a mass shift from one or more post-translational modifications.

Base peak testing involves comparing a mass of a theoretical ion of the sample to the mass of a base peak. Samples having theoretical ions having a mass that matches the mass of the base peak can be further processed. Samples having theoretical ions having a mass that does not match the base peak can be discarded from further consideration, and the next sample is assessed. Referring FIG. 6A, the tallest spectra line is considered "the base peak" and is centered around 200 daltons as per the horizontal axis. In contrast to the subject matter disclosed herein, many conventional methods begin the identification process with the base peak and look up and down spectra to establish an identification. In some embodiments disclosed herein, the base peak value can be used as part of a rapid pass fail test. Both the precursor mass and base peak values are provided directly by the instrument to avoid the computational load of processing the entire set of spectra lines. This permits testing the random peptides rapidly on modestly priced computing systems.

Base peak testing can involve the processor 112 determining a mass of a theoretical ion of the sample. If the mass of the theoretical ion is substantially equal to a mass of a base peak, the processor 112 can select that sample for comparison with one or more candidate peptide sequences.

In some embodiments, if the precursor mass is not present in the observed spectra, the precursor mass can be added to the theoretical spectra. By adding the precursor mass to the theoretical spectra, the likelihood of identifying the first amino acid in the peptide sequence is increased and the Amino Acid Match Ratio (AAMR) score can be improved. Fragmentation is a two-step process. First an MS1 scan is taken, which establishes the precursor mass. An MS2 scan is then taken. Ideally, this precursor mass would also appear in the MS2 spectra at the far right of the spectra. However, in practice, this precursor mass may not be present in the MS2 spectra as an amino acid may have been "lost" between the MS1 and MS2 scans. If the precursor mass is not present in the MS2 scan, it can be added. The missing amino acid would appear at the start of an identified peptide. For example, in tests on Angio tension peptide DRVYIHPF, the first amino acid D is often lost.

In some embodiments, a theoretical ion can be added to the theoretical spectra, that is the low end of the spectra can be added to. The theoretical ion can represent a terminal mass. Addition of the theoretical ion can improve the peptide match mass ratio score. Similar to injecting a precursor mass into the high end of the spectra, a terminal mass can be injected at the low end of the spectra. The terminal mass is not an amino acid but rather a chemical structure that exists at the end of a natural peptide. As discussed elsewhere there are two fragmentation patterns Y and B, with the Y chain starting at the high end or right most spectra where a precursor mass can be injected while the B chain analysis starts at the low end or left most spectra. The terminal mass is often not captured by the mass spectrometer as its mass is lower than the instrument can detect. By artificially injecting this terminal mass, this mass can be used as a starting point and look upwards in the spectra for the amino acid from the B chain. Using angiotensin as an example with the peptide sequence DRVYIHPF, this would identify the last amino acid F, being the last amino acid fragmented before reaching an either real or artificially injected Terminal Mass ion.

In some embodiments, a theoretical peptide's MH value at charge state 1, or 2 or 3 could be added to the theoretical spectra. Addition of the theoretical peptide's MH value at charge state 1, or 2 or 3 can apply to the peptide match score. Once a random peptide is generated, both the theoretical spectra and MH value can be calculated. The MH mass can be compared to the precursor mass so as to calculate the peptide's charge. The mass spectrometer however, regardless of the precursor mass may well be reporting the spectra for a peptide at each of the three charge states within a single MS2 scan. If this is the case, then the real 1+ spectra representing the unknown peptide can generally provide the most usable spectra. In some embodiments, the 1+ spectra can be used as the primary identification signal followed by examination of the 2+ and 3+ spectra for additional evidence of a good identification.

In some embodiments, the MH of a particular peptide can be injected into the observed spectra. Addition of the MH of a particular peptide can be used to calculate the peptide match score.

In some embodiments, the difference in theoretical mass and the observed peptide mass can be calculated using the estimated charge of a theoretical peptide, the known theoretical mass of the same theoretical peptide, and the known observed precursor mass. The delta mass can be used to identify a modification which is an extra chemical element on the peptide. This is also known as a modification mass. For example, phosphorylation is a commonly observed post translational modification and has a known mass shift of 79.99 Da; if the delta mass is about this value, then it can be determined that the peptide is phosphorylated. Such modifications are relevant to the role a peptide may play with respect to human health as the presence of this element shows in the precursor mass but is not part of the theoretical mass, and also may not appear in the MS2 spectra. This delta mass value is then highly suggestive of some modification. To test for a modification, the modification mass is subtracted from the precursor mass. If the results of this calculation match the theoretical mass of the random peptide and the real MS2 spectra matches the theoretical spectra, it can be assumed that there is a theoretical peptide and a modification.

In some embodiments, application of signal processing filters can vary. For example, in some embodiments, only minimum spectra counting can be used. In other embodiments, minimum spectra counting, maximum spectra lines filtering, sequential ion (e.g., b and y ions) counting, and precursor testing can be used. Other combinations are possible. Furthermore, the signal processing filters can also depend on whether a candidate peptide sequence is selected from memory or randomly generated.

Figure 5A:
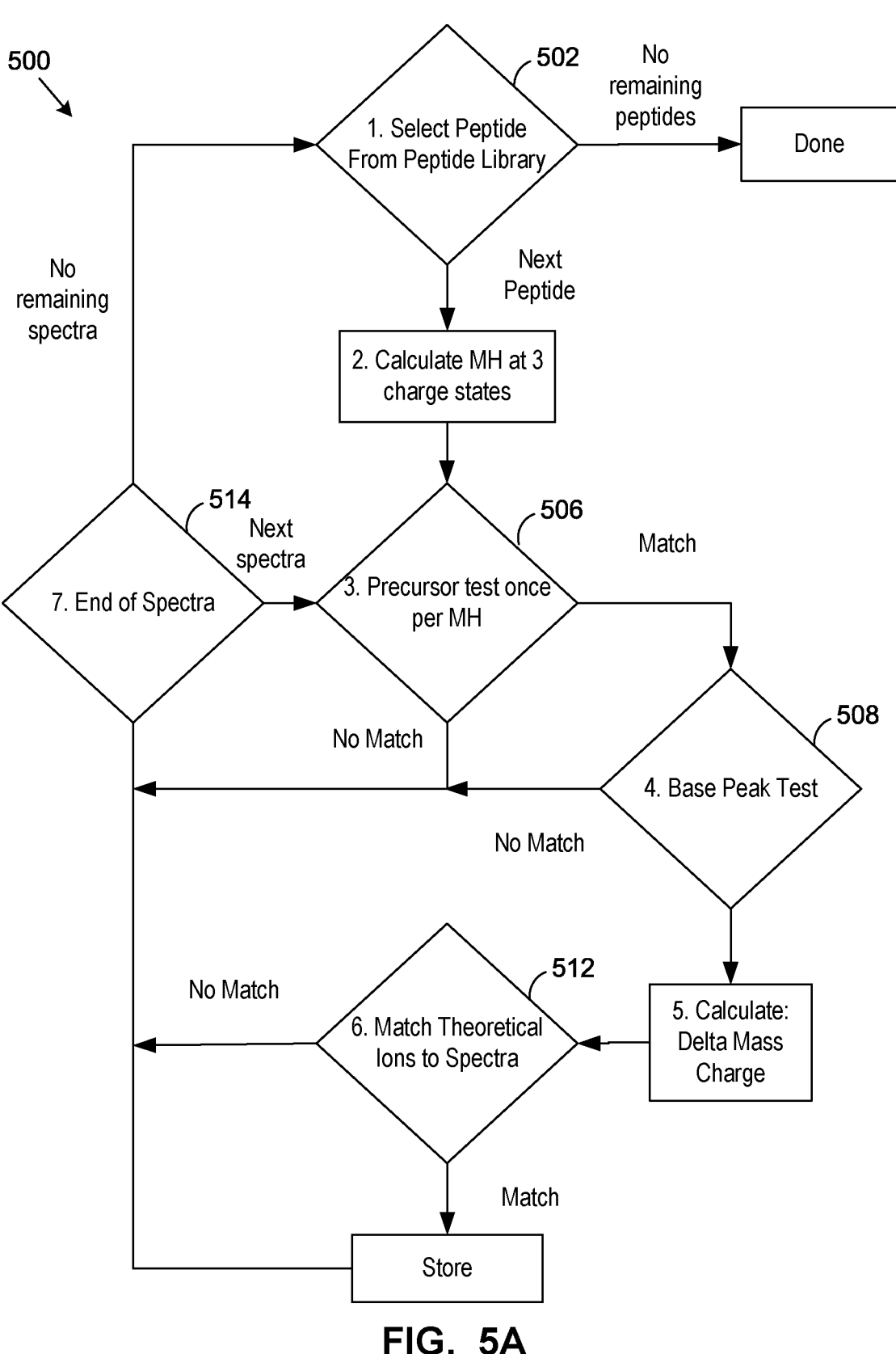
FIG. 5A is a flowchart for selecting samples for comparison with candidate peptide sequences selected from memory, in accordance with an example embodiment.

Reference is now made to FIG. 5A, which shows a flowchart 500 for selecting samples for comparison with candidate peptide sequences selected from memory. As shown in flowchart 500, the theoretical peptide list, that is the list of candidate peptide sequences, is contained in an outer loop 514 and each sample, such as a MS/MS spectra, in an inner loop. One theoretical peptide or candidate peptide sequence at a time 502 is compared to all available scans by tests and scoring algorithms until the peptide list is exhausted. In this embodiment, each theoretical peptide and spectrum pair must pass a precursor mass test 506 and base peak test 508 before they are scored by at least one of chi square, multiple/linear or nested regression, amino acid match ratio, and ion intensity match ratio. A user defined combination of these scores can be used to identify the best match for each scan 512.

In other embodiments, the loops can also be nested in the opposite fashion. That is, one sample is compared to each candidate peptide sequence before another sample is compared to each candidate peptide sequences.

Figure 5B:
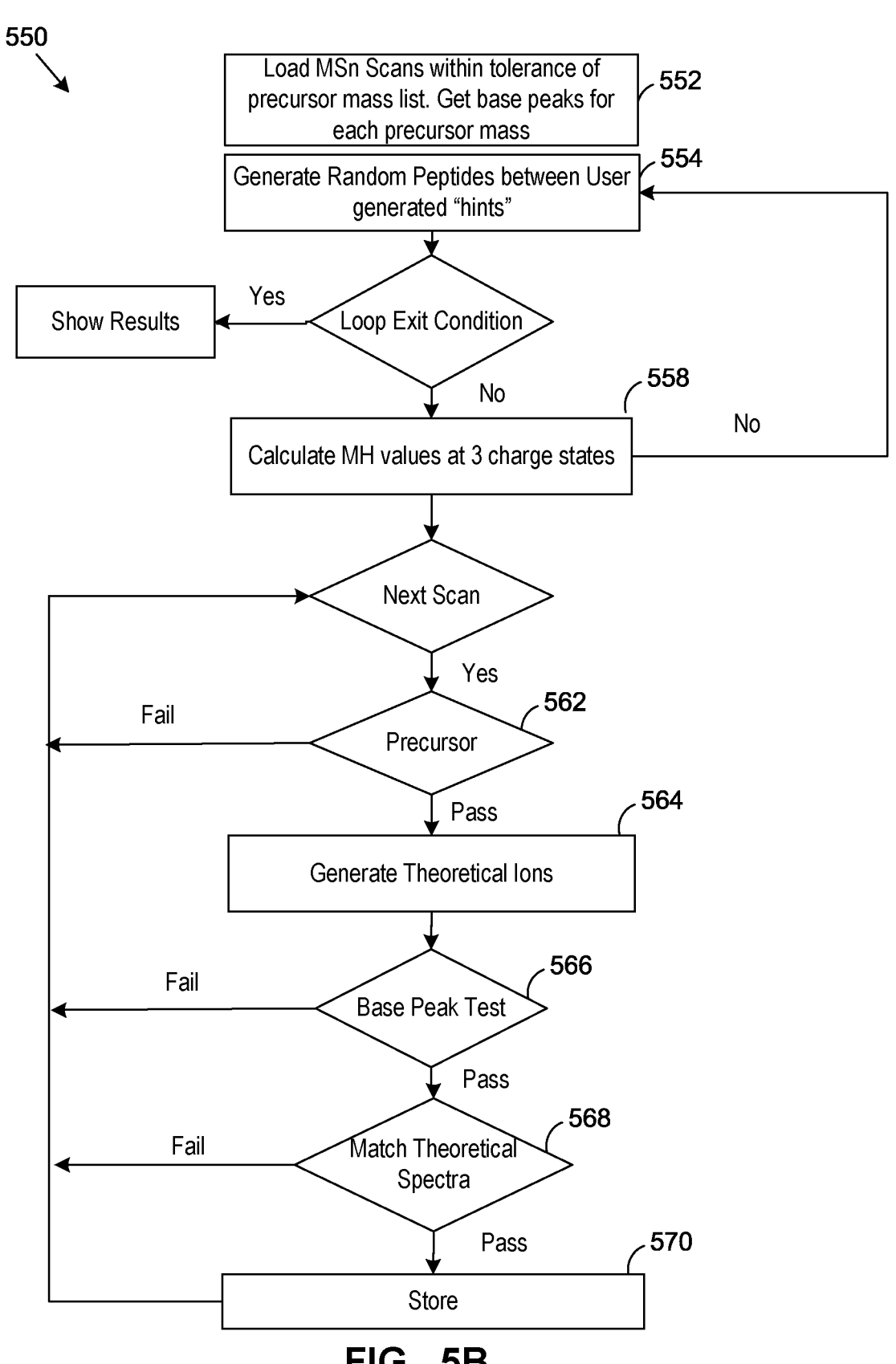
FIG. 5B is a flowchart for selecting samples for comparison with randomly generated candidate peptide sequences, in accordance with an example embodiment.

Reference is now made to FIG. 5B, which shows a flowchart 550 for selecting samples for comparison with randomly generated candidate peptide sequences. As shown in flowchart 550, a "first in first out" (FIFO) queue of candidate peptide sequences can be used instead of an outer loop of flowchart 500. The queue grows as candidate peptide sequences are generated and shrinks each time a candidate peptide sequence is processed.

Constraints can be used to narrow the possible combinations for randomly generated candidate peptide sequences. Constraints can be specified by the user, that is a parameter received from computing device 120. Constraints can also be determined from the library search method or from amino acid matching. As set out above, constraints can relate to a pre-determined length, a minimum number of amino acids from different amino acid groups, a particular amino acid at a particular position, and/or a precursor mass.

In the example shown in flowchart 550, a constraint relating to the precursor mass is used. At 552, the processor 112 can retrieve all samples, such as MSn scans, having a precursor mass within a tolerance window and create a list of the base peak values from these scans. The processor 112 can randomly generate a candidate peptide sequence based on a pre-determined length and wild cards 554, and then generate the MH value of that candidate peptide sequence at each of 3 charge states 558. The processor 112 can run the precursor test 562 to the candidate peptide sequence and if passed, the processor 112 can generate the theoretical spectra 564 and run the base peak test 566. If the base peak test is passed, the more computationally intensive AAMR and IIMR tests are run 568. If these last two scores are above minimum thresholds, then the candidate peptide sequence is considered a match and is stored 570.

The precursor and base peak tests can be repeated again later in the workflow due to technical reasons. In particular, the precursor hint can be a list of m/z values so one candidate peptide sequence might not match at the precursor at the precursor level for a particular scan, and similarly it may not pass the base peak test.

Returning now to FIG. 2, at 218, the processor 112 can determine, based on the one or more test results, a likelihood indicator for each candidate peptide sequence based on a comparison with the at least one sample.

In some embodiments, determining a likelihood indicator for each candidate peptide sequence can involve applying scoring techniques, filtering techniques or a combination thereof. For example, scoring techniques can first be applied. The scoring techniques can be analogous to the signal processing filters applied at 216, including spectra line filtering.

The likelihood indicator can alternatively or additionally be determined based on additional filtering techniques including one or more of a chi-square score, a regression score, and a cross correlation score. Other scoring functions can be used to generate a likelihood indicator.

In some embodiments, a chi-square score can be used to rank candidate peptide sequence matches. For example, a candidate peptide sequence can be selected as a proposed peptide sequence based on differences between an observed ion count of the candidate peptide sequence and the predicted theoretical ion count.

Chi-square can be applied to the m/z values of observed and expected spectra lines for all matching ions as described by Equation (1) where the smallest score is highest ranked (i.e., wins):

$$\chi2 = \frac{(ObsMz1 - ExpMz1)^2}{Exp1Mz} + \frac{(ObsMz2 - ExpMz2)^2}{Exp2Mz} \dots + \frac{(ObsMzn - ExpMzn)^2}{ExpNMz}$$

Equation (1)

Figure 6A:
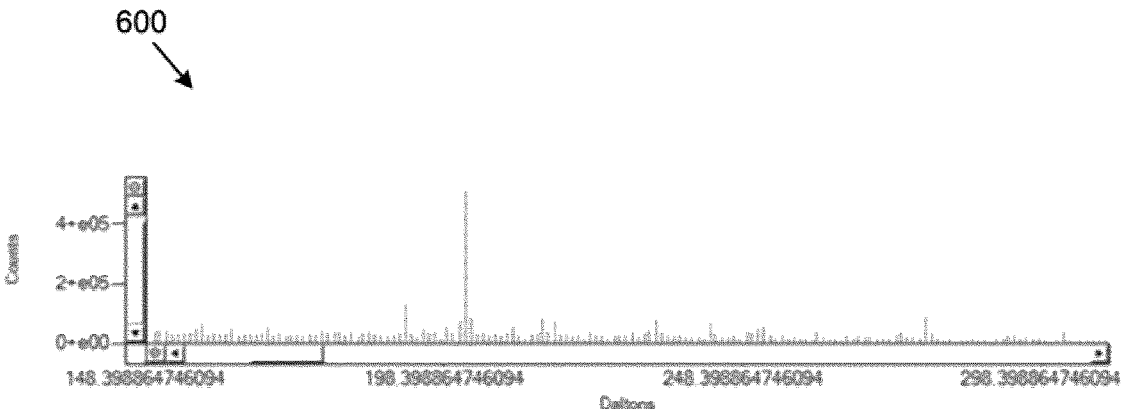
FIG. 6A is an illustration of a spectrum, in accordance with an example embodiment.
Figure 6B:
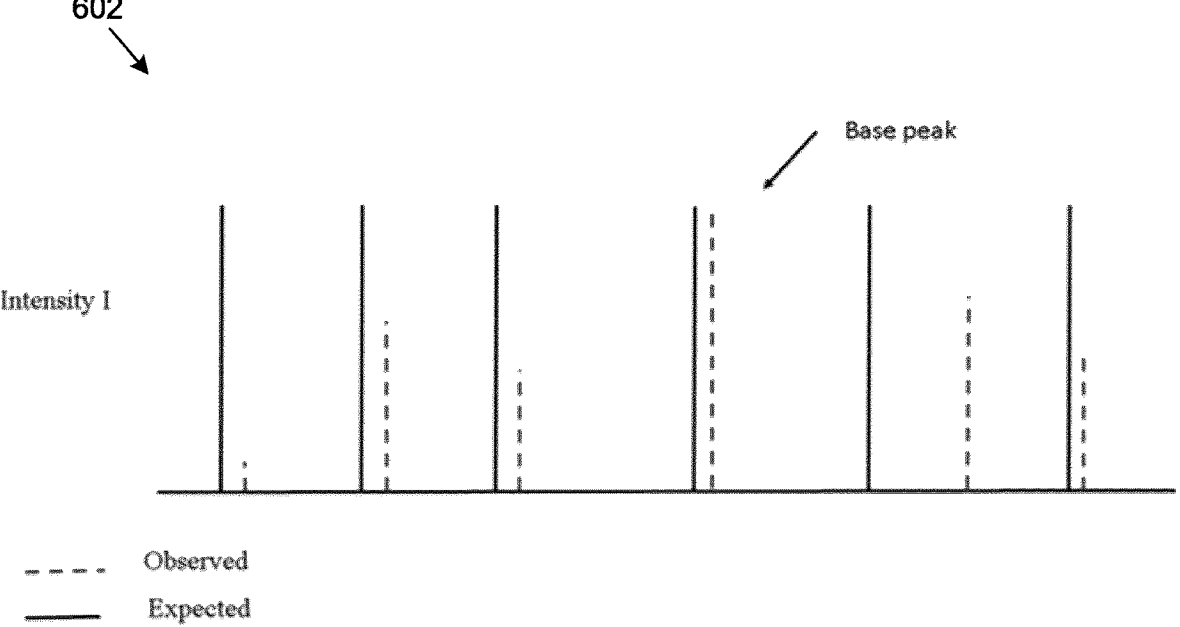
FIG. 6B is an illustration of m/z values of observed and expected spectra lines for matching ions, in accordance with an example embodiment.

FIG. 6B is an illustration of the m/z values of observed (shown in dashed lines) and expected (shown in solid line) spectra lines for matching ions. All of the expected spectra lines form the base peak.

Alternatively, the chi-square score can be calculated by summing the number of expected theoretical ions (e.g., b and y ions) for the expected peptide that fall within the M/z range of the mass spectrometer; summing the number of observed ions that match the expected M/z values, within the mass resolution limit of the mass spectrometer and applying Equation (2).

$$\chi2 = \frac{(ObsMz - ExpMz)^2}{ExpMz + 1}$$

Equation (2)

In some embodiments, prior to applying Equation (2), a correction can be applied to the expected theoretical ion count. A correction can be applied to compensate for the M/z range and/or mass error of the mass spectrometer. In some embodiments, applying the correction involves multiplying the expected theoretical ion count by the total number of observed ions and dividing the product by the number mass spectrometer bins. The number of bins can be determined according to Equation (3).

$$Number\ of\ bins = \frac{Range}{Resolution}$$

Equation (3)

For example, for a mass spectrometer with a range of 50 to 2000 M/z units and a mass resolution of +/−0.5 M/z units, the number of bins is equal to 2000-50/(0.5−(−0.5)=1950.

Various regression methods can be used to generate a likelihood indicator in some embodiments. Linear regression can be used to generate a simple linear regression model for each candidate peptide sequence to identify the best fitting model. Multiple linear regression can also be used to incorporate additional explanatory variables into the model such as intensity.

In some embodiments, cross correlation can be used to generate a likelihood indicator. The processor 112 can determine a cross correlation score of a sample relative to a candidate peptide sequence. For example, a scoring function can measure the similarity of an MS/MS spectra relative to a theoretical spectrum. Cross correlation can use a sliding dot product. Although cross correlation can be computationally expensive, various methods can be employed to reduce the computational cost.

A method of determining a cross correlation score can involve first assigning an intensity to theoretical b ions and y ions. The square root of the ion intensities of the observed b and y ions is then calculated. The mean of the cross correlation over 500 lags is then calculated and subtracted from the cross correlation between the observed and theoretical ions at a lag of 0. Other methods of determining a cross correlation score can be used, such as the method described in Eng, J. K., McCormack, A. L., & Yates, J. R. (1994). "An approach to correlate tandem mass spectral data of peptides with amino acid sequences in a protein database. Journal of the American society for mass spectrometry", 5(11), 976-989.

Other scoring functions can also be used, such as an ion intensity match ratio (IIMR), or an Amino Acid Match Ratio (AAMR).

As described, the ion intensity match ratio (IIMR) can generate a signal to noise score for each theoretical peptide match. The ion intensity match ratio can be calculated from the sum of ion intensities where there is a match to the theoretical spectra and is divided by the total sum of the ion intensities in the observed spectra. The IIMR value ranges from 0 to 1, in which 1 represents a perfect score and corrects for duplicate ion matches.

It is noted that the signal processing filters previously mentioned may have already reduced the noise. Since the ion intensity match ratio is determined after the signal processing filters have been applied, the ion intensity match ratio can be based on the Total Ion Current (TIC) for that spectrum. That is, the IIMR can be determined by dividing by the TIC for that spectrum.

The Amino Acid Match Ratio can be used to generate an ordered list of suspected amino acids in the peptide by comparing the m/z differences in pairs of observed spectra lines.

The Peptide Match Ratio can be calculated by taking the sum of the correctly ordered amino acids and dividing that sum by the total number of amino acids used to generate the theoretical spectra. Since the Peptide Match Ratio score is computationally expensive, the Peptide Match Ratio may be only run against the best scoring results.

Independent scoring algorithms can also be used to generate a single vector using Equation (4). The single vector can be more computationally efficient.

$$c = \sqrt{(a^2 + b^2)}$$

Equation (4)

Neutral Loss ions and A ions can be considered diagnostic or confirmatory ions which contribute to a score. Ion pairs, which can identify an Amino Acid as described in the Peptide Match ion, can represent a secondary scoring mechanism related to these confirmatory ions.

At 220, the processor 112 can apply a signal-to-noise filter to the one or more candidate sequences based on the likelihood indicators for the candidate peptide sequences.

Mass spectrometers, even without a sample, continuously generate source noise spectra. A signal-to-noise filter can be applied using a Monte Carlo random simulation to separate real data from random spectra by chi-square or other statistical means. The signal-to-noise filter can eliminate samples that show minimal significance when compared to random or source noise spectra. The random source noise can be generated either with blank solvents applied to naïve columns or using random number generators. Peptide sequences matching to random MS/MS spectra at high frequency compared to real data by chi square or other statistical means are not carried forward for further analysis.

In some embodiments, the processor 112 can generate random source noise spectra at high frequencies. The processor 112 can determine a difference between the random source noise spectra at high frequencies to the one or more candidate peptide sequences. If the difference does not exceeds a pre-determined threshold difference, the sample can be excluded from selection as a proposed peptide sequence for the query spectrum. Otherwise, the sample can be selected as a proposed peptide sequence.

At 222, the processor 112 can select a candidate peptide sequence as a proposed peptide sequence for the query spectrum based on the filtered candidate peptide sequences. The selection of proposed peptide sequences from filtered candidate peptide sequences can be based on a best fit. The fit can relate to a peptide, accession, or gene symbol. In some embodiments, a machine learning model can be used to select the best fitting filtered candidate peptide sequence to the proposed peptide sequence. As shown in FIG. 2B, in some embodiments, a protein 250 containing the identified peptide can be identified.

While in FIG. 2A, step 220 is shown as preceding step 222, in some embodiments, step 220 can be omitted and the processor 112 can select a candidate peptide sequence as a proposed peptide sequence for the query spectrum from the candidate peptide sequences filtered using the fitting algorithms (e.g., chi-square, linear regression, cross-correlation, etc.). In such embodiments, the processor 112 can apply a signal to noise ratio filter similar to step 210 to the proposed peptide sequence. For example, the processor 112 can count the number of spectra in the sample that match the proposed peptide sequence and compare this count to a count for randomly generated and/or experimentally obtained spectra (e.g., inauthentic). The processor 112 can exclude from further analysis samples associated with counts that are similar to those of inauthentic samples.

Figure 6C:
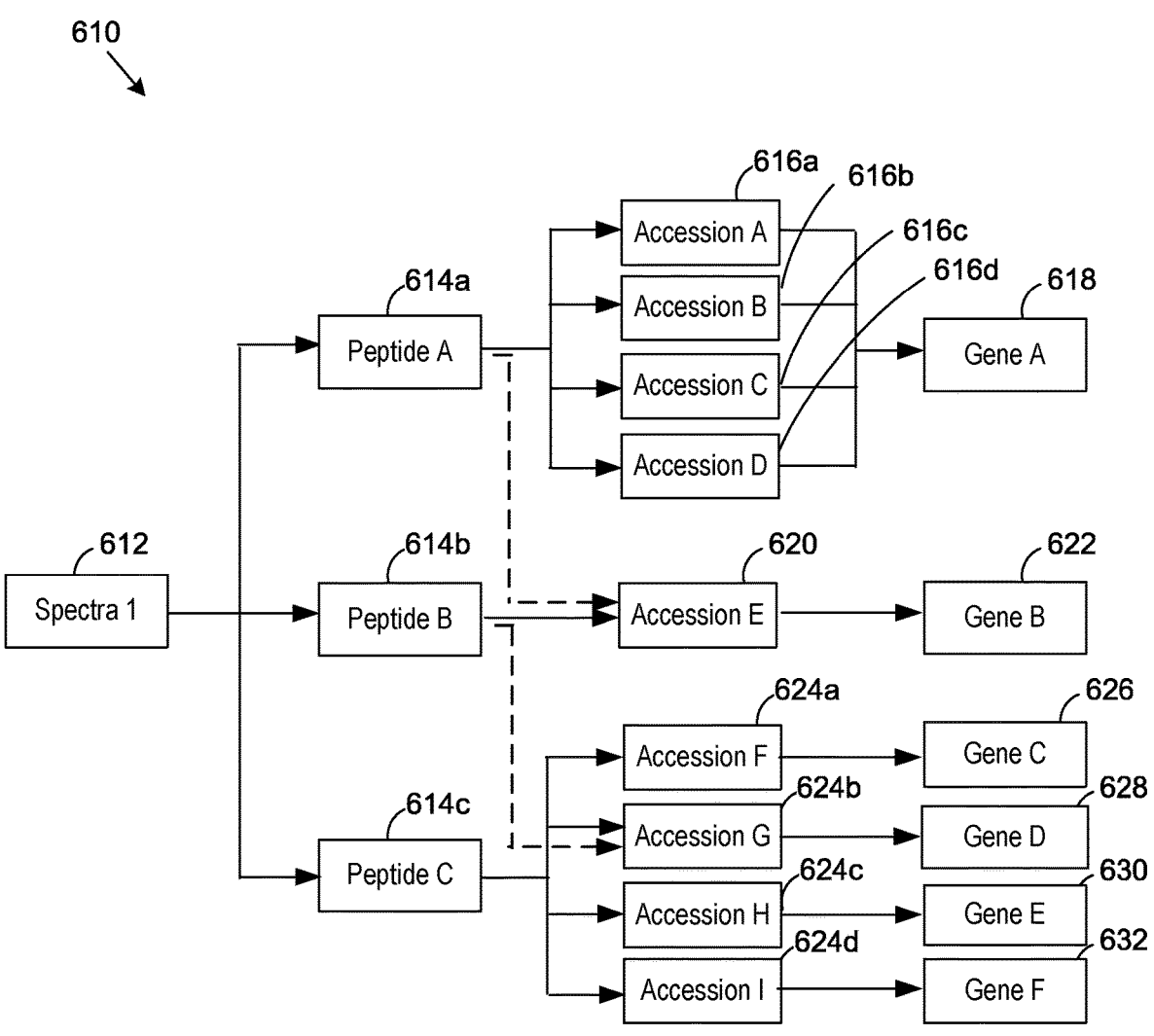
FIG. 6C is an illustration of possible relationships between peptides, accessions, and gene symbols, in accordance with an example embodiment.

A challenge with mass spectrometry relates to generating non-redundant datasets for analysis. This challenge can be due to the nature of how peptides, accessions and gene symbols map to one another. FIG. 6C illustrates an example mapping 610 of the relationship between peptides, accessions, and gene symbols. As shown in FIG. 6C, an MS/MS spectrum 612 (e.g., Spectra 1) can map to multiple peptides 614a, 614b, 614c (e.g., Peptide A, B, and C, respectively). Each peptide can map to multiple accessions. For example, peptide 614a (e.g., Peptide A) can map to multiple accessions 616a, 616b, 616c, 616d, and 620 (e.g., Accession A, B, C, D, and E respectively); peptide 614b (e.g., Peptide B) can map to accessions 620 and 624b (e.g., Accession E and G), and peptide 616c (e.g., Peptide C) can map to multiple accessions 624a, 624b, 624c, and 624d (e.g., Accession F, G, H, and I respectively). Accessions can map to different gene symbols. For example, accession 624a (e.g., Accession F) can map to gene 626 (e.g., Gene C); accession 624b (e.g., Accession G) can map to gene 628 (e.g., Gene D); accession 624c (e.g., Accession H) can map to gene 630 (e.g., Gene E); and accession 624d (e.g., Accession I) can map to gene 632 (e.g., Gene F). Accessions can also map to the same gene symbols. For example, accessions 616a, 616b, 616c, and 616d (e.g., Accession F, G, H, and I respectively) can map to gene 618 (e.g., Gene B). As can be seen in the example of FIG. 6, the relationship between peptides, accessions, and gene symbols can lead to highly redundant data.

One or more strategies can be employed to reduce the redundancy of the final data without a loss of information at the level of peptides, accessions, and gene symbols.

For example, one strategy can involve assigning a unique identifier to each sample or MS/MS spectrum (e.g., spec-traID) and selecting the best fit per spectrum (BFPS) for each sample or MS/MS spectrum. The best fit can be determined by the likelihood indicator. In some embodiments, the best fit can be determined using a machine learning model.

Candidate peptide sequences can be generated by multiple combinations of methods, including multiple libraries and multiple random generation methods. A unique identifier can be assigned to each combination (e.g., search definition ID). There can be different approaches to calculating a best fit. In some embodiments, a best fit can be calculated by search definition ID, where for each search definition ID, a best fit per spectra is chosen independently of the other search definition IDs.

In some embodiments, the best fit per spectrum (BFPS) can be selected by Library and Search Engine. In the case where there are multiple static search methods for one library engine combination, the counts may be split off into the method where the spectraID scored the best, or had the highest likelihood indicator. In this case there is minimal overlap between the two methods except where the spectraID scored equally highest in both methods. Once the best fit per spectrum is identified, a non-redundant list can be made for each level that the data may be analyzed.

At the level of gene symbols, only unique SpectralID-SearchdefinitionID-Genesymbol combinations are carried forward to create counts for all the subgroups for the experiment and are used for further statistical analysis where groups are compared by gene symbol.

The same is done at the level of peptides, where only SpectralID-SearchdefinitionID-Peptide combinations are carried forward for count tables and analysis at the level of peptides. Seachdefinition ID corresponds to the library and search settings.

The peptide identification system 110 was tested using samples of angiotensin and GluFib, samples of 18 standard proteins, and samples of plasma. The results were compared with existing systems, such as X!Tandem, Sequest® (Proteome Discoverer).

For the angiotensin and glufibrinogen (GluFib) test, single peptide standards of angiotensin and GluFib were prepared. A dilution series of GluFib and angiotensin from 0.1, 5, 10, 50, 100, 500, 1000 ug/mL were applied to a LTQ linear ion trap by direct infusion. That is, the two peptide standards, angiotensin and GluFib, were injected into the mass spectrometer at increasing concentrations from 0 ug/mL to 1000 ug/mL resulting in 16 MS runs per standard including replicates. The peptide sequences for these two standards are DRVYIHPF for Angiotensin and EGVNDNEEGFFSAR for GluFib.

The peptide identification system 110 was able to identify Angiotensin and GluFib peptides with identification counts increasing by concentration. For the random generation method, the peptide identification system 110 was given constraints of 523 and 1046 Daltons and for demonstration purposes, a peptide constraint of D*VYIHPF. From these constraints, the system generated four candidate peptides: DFVYIHPF, DRVYIHPF, DUVYIHPF and DYVYIHPF and subsequently proposed only the angiotensin standard peptide DRVYIHPF.

For the library selection method, the peptide identification system 110 used two peptide libraries for each sample. For the angiotensin sample test, the first library stored only angiotensin peptides and the second library, containing 200 peptides in total, stored angiotensin peptides and hundreds of other peptide sequences taken from human and other species where the mass of the peptide was very close to the known masses of the sample angiotensin peptide at various charge states. Similarly, for the GluFib sample test, the first library stored only GluFib peptides and the second library, containing 232 peptides in total, stored GluFib peptides and hundreds of other peptide sequences taken from human and other species where the mass of the peptide was very close to the known masses of the sample GluFib peptide at various charge states.

The peptide identification system 110 using candidate peptide sequences selected from memory identified angiotensin peptide DRVYIHPF 638 times across all angiotensin samples with a select number shown with their scores, or likelihood indicators, as shown in table 700 in FIG. 7A. Analysis of the spectra of one high concentration angiotensin peptide suggested that 114 charge 1 identifications and 24 charge 2 identifications should be expected. The results indicated 114 charge state 1 identifications and 14 charge state 2 identifications.

Similarly, the GluFib peptide direct spectral analysis suggested that 76 charge state 1 peptide identifications and 76 charge state 2 identifications should be expected. The results indicated 76 charge state 1 identifications and 75 charge state 2 identifications. Accordingly, the systems and methods disclosed herein correctly identified the angiotensin and glufibrinogen peptides.

In contrast, the existing systems X!Tandem and Sequest® performed poorly when set to a no-enzyme search. In particular, X!Tandem returned no identifications over the set of run and Sequest® returned 1 GluFib identification. It is noted that X!Tandem and Sequest® were not searched against limited libraries containing only angiotensin or only GluFib and other peptide sequences with similar mass.

Figure 7C:
FIG. 7C is a table of likelihood indicators for various candidate peptide sequences for a given query spectrum accounting for charge state, in accordance with an example embodiment, said table comprising the following sequences: EGVNDNEEGFFSAR (SEQ ID NO: 1), EYGLPAVVGVE-HATK (SEQ ID NO: 15), TLYYAR (SEQ ID NO: 16), GAIVAIMTOPSANDGK (SEQ ID NO: 17), ADVOGS-VEALAAALOK (SEQ ID NO: 18), ADISIPIMVG-GAALSR (SEQ ID NO: 19), ALQIVSR (SEQ ID NO: 20), and GAPAIMKPFEEILR (SEQ ID NO: 21)

The peptide identification system 110 using candidate peptide sequences selected from memory identified the GluFib peptide EGVNDNEEGFFSAR 868 times across all angiotensin samples with a select number shown with their scores as shown in table 720 in FIG. 7B. Furthermore, GluFib peptide EGVNDNEEGFFSAR was both the top scoring peptide and third best scoring after accounting for charge state as shown in the in table 740 FIG. 7C.

For the 18 standard proteins test, a set of 18 standard peptides were applied to both nano and micro electrospray as previously described. Each sample was injected twice and come from 9 different species.

The 18 standards proteins are from nine species. As such, for the library selection method, one protein library was assembled for each species containing only the protein standards belonging to that species. A small library containing the 18 proteins which the protein standards were expected to contain was also produced. All samples were run against the small 18 protein library and against the species library appropriate to the sample.

As the 18-protein library is small there in turn is a modest number of digested peptides and therefore limited competition between peptides for high quality identifications for a particular line of MSn Spectra.

Referring now to FIG. 8A, FIG. 8B, and FIG. 8C shown therein are graphs 800, 810 and 820, respectively, showing the results of the 18 standard proteins test from the peptide identification system 110, X!Tandem, and Sequest® (Proteome Discoverer), respectively. In graphs 800, 810 and 820, the vertical axes show the identification count and the horizontal axes show the Gene symbols listed alphabetically. A black column indicates identifications where the candidate peptide sequence matched the sample, while the red lines indicate where the candidate peptide sequence did not match the sample.

As can be seen in FIG. 8A, FIG. 8B, and FIG. 8C, the peptide identification system 110 and the existing systems performed well in the 18 standard proteins test. Furthermore, the peptide identification system 110 was able to make accurate identifications that were functionally comparable to existing systems.

Figure 9A:
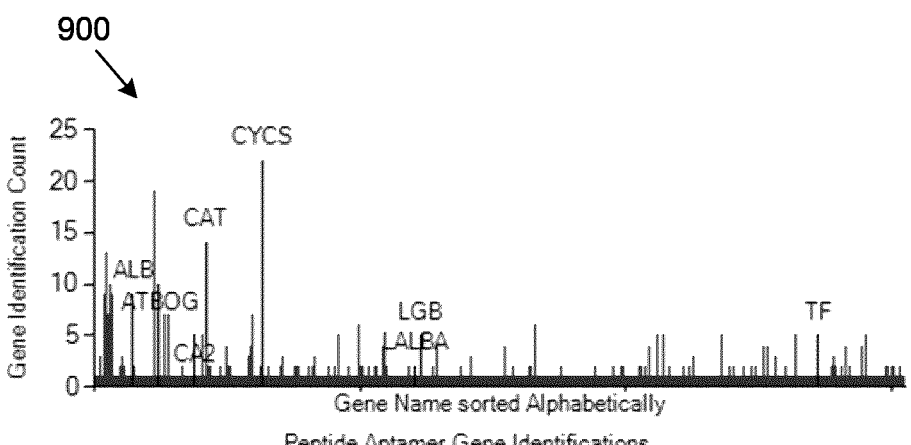
FIG. 9A is an illustration of results of 18 standard proteins test from a peptide generation system using a *Bos taurus* protein library, in accordance with an example embodiment.
Figure 9B:
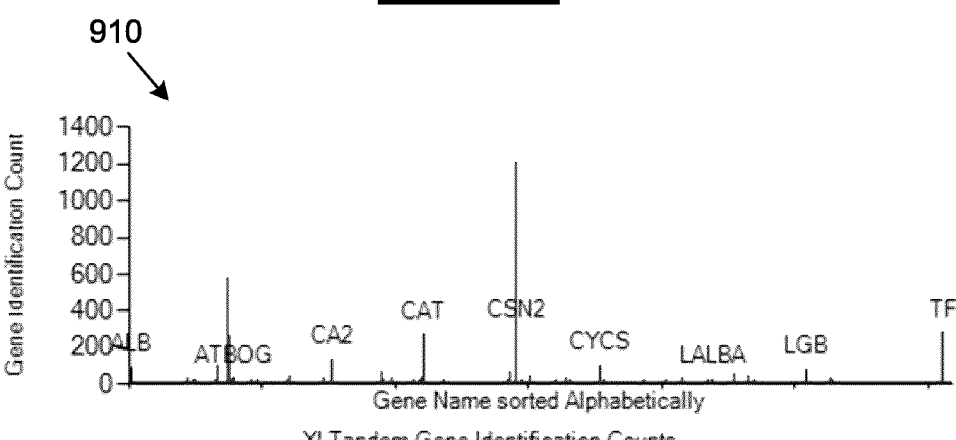
FIG. 9B is an illustration of results of 18 standard proteins test from an X!Tandem system using a *Bos taurus* protein library.
Figure 9C:
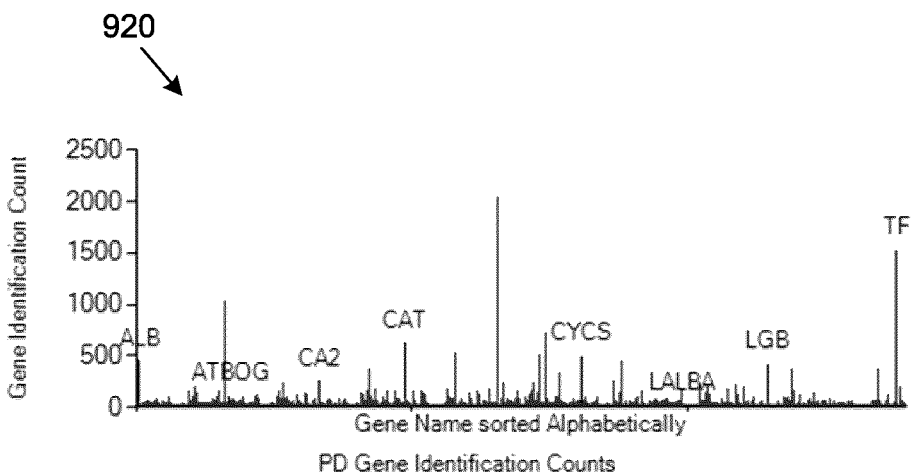
FIG. 9C is an illustration of results of 18 standard proteins test from a Sequest® (Proteome Discoverer) system using a *Bos taurus* protein library.

Searching against a full species library can test a system's ability to attribute each scan to the correct theoretical peptide given much larger competition. Graphs 900, 910 and 920 shown in FIG. 9A, FIG. 9B, and FIG. 9C, respectively, show the same set of runs as graphs 800, 810 and 820 shown in FIG. 8A, FIG. 8B, and FIG. 8C, respectively, but against a typical b. Taurus library containing 160297 distinct proteins yielding 5,285,355 peptides after in-silico digest with 0 missed cleavages. As can be seen, the results of the peptide identification system 110 when used with a large protein library are similar in quality (but not quantity) to existing systems.

Table 1 shows the number of distinct peptides where a system returned a peptide actually present in the reference protein library, which was in-silico digested with 0 missed cleavages and where the reported protein accession number matches that in the library. Based on the number of exact identifications that each system returned, the peptide identification system 110 more accurately identifies the presence of specific peptides.

TABLE 1

| Search Engine | Exact identifications against library |
|---|---|
| X!Tandem | 832 |
| Sequest ® (Proteome Discoverer) | 0 |
| Peptide identification system 110 | 376536 |

For the plasma test, a total of 12 plasma 25 uL samples were sterilized with 250 μL of 100% acetonitrile (HPLC grade), centrifuged at 14,800 rcf for 5 minutes. The supernatant was removed, and the sample freeze dried overnight. The freeze-dried plasma samples were resuspended in 200 μL of 20 mM Tris, pH 8.8 loading buffer, applied to a QA column containing 100 μL of resin, washed in 3 volumes of loading buffer and eluted in 200 μL of 300 mM NaCl in 20 mM Tris pH 8.8. The Resin was collected in 200 μL of loading buffer. The QA salt extracted fractions divided into three subgroups of 4 samples and digested by either: 1. tryptic digest and partial reduction, 2. tryptic digest with reduction and alkylation, 3. tryptic digest without reduction or alkylation. The samples were applied to nano-LC-MSMS.

Figures 10A, 10B, 10C:
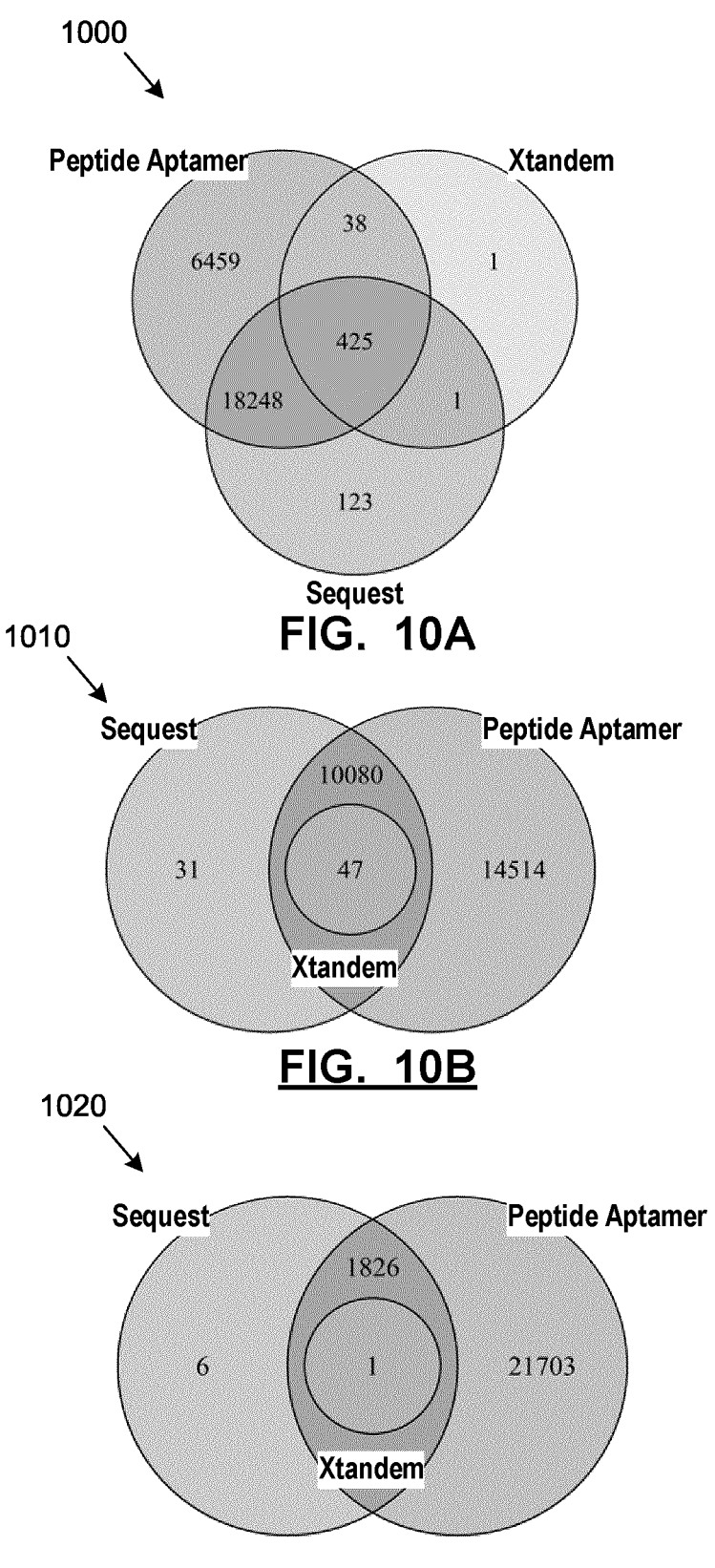
FIGS. 10A, 10B and 10C are overlapping gene symbols identified between peptide aptamer, X!Tandem and Sequest® using three different thresholds.

Referring now to FIG. 10A, FIG. 10B, and FIG. 10C, shown therein are diagrams 1000, 1010, 1020, respectively, showing results of the plasma test, namely the gene symbols identified against the tryptic human library by the peptide identification system 110 and the existing systems. FIG. 10A shows the overlapping gene symbols with at least 1 peptide count and no missed cleavages; FIG. 10B shows the overlapping gene symbols with at least 3 peptide counts and no missed cleavages; and FIG. 10C shows the overlapping gene symbols with at least 10 peptide counts and no missed cleavages.

The peptide identification system 110 can use two sources of theoretical ions-either the random generator or a known theoretical spectra library. The dual nature of the peptide identification system 110 can be advantageously utilized in numerous ways. First, use of the spectra library to identify the best matching peptide sequence followed by the random generator where combinations of the same amino acid sequence plus possible modifications are randomly generated until the most optimal fit is obtained.

Second, where one source of theoretical spectra is used to fill in some amino acid gaps under a certain set of criteria, then peptide identification system 110 can automatically switch to the other source of theoretical spectra given certain thresholds or parameters. Third, synthetic peptide libraries can be generated to include known amino acids at known positions, or based on partial sequences known to bind a target binding site for example that reduce the number of possible randomly generated peptides. Fourth, peptide sequences can be excluded from the random generator pool of possibilities. In addition, parameters can be set to change the random generator strategy based on certain events, thresholds or parameters.

Figure 11A:
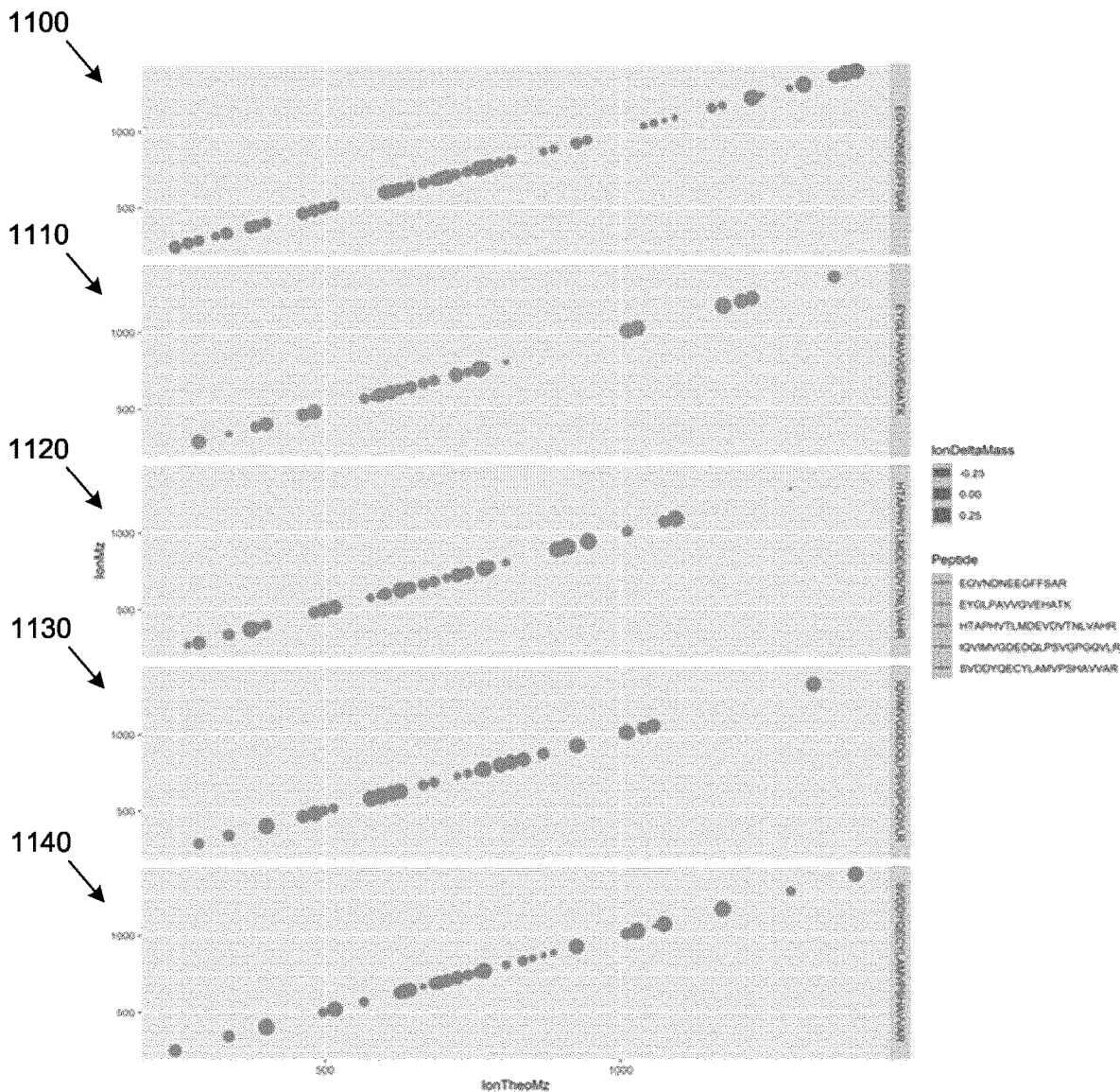
FIG. 11A is an illustration of linear regression models to fit a query spectrum to various candidate peptide sequences, in accordance with an example embodiment.

Referring now to FIG. 11A, shown therein is an illustration of linear regression models to fit a query spectrum to various candidate peptide sequences, in accordance with an example embodiment. Fragment ions of a spectrum were fit against the theoretical MS/MS ions of five candidate peptide sequences 1100, 1110, 1120, 1130, 1140, and 1150. In FIG. 11A, the actual versus theoretical m/z values for each candidate peptide sequence is shown and the size of each dot indicates the difference between actual and theoretical mass. FIG. 11B shows a table 1160 showing the data of the linear regression models for each candidate peptide sequence of FIG. 11A (i.e., the first row containing results corresponds to candidate peptide sequence 1100, the second row corresponds to candidate peptide sequence 1110, the third row corresponds to candidate peptide sequence 1120, the fourth row corresponds to candidate peptide sequence 1140 and the fifth row corresponds to peptide sequence 1150) Based on these fits, one candidate peptide sequence (EGVND-NEEGFFSAR) could be identified as the best fit.

Figure 12A:
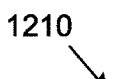
FIG. 12A is a table showing results of different fitting methods for a EGVNDNEEGFFSAR (SEQ ID NO: 1) glufib peptide, searched against a small cow library and reduced to the top 30 gene symbols, with filters, in accordance with an example embodiment.
Figure 12B:
FIG. 12B is a table showing results of different fitting methods for a EGVNDNEEGFFSAR (SEQ ID NO: 1) glufib peptide, searched against a small cow library and reduced to the top 30 gene symbols, without filters, in accordance with an example embodiment.

As described, various regression models can be used to fit a query spectrum. Referring now to FIGS. 12A-12B, shown therein are tables 1210 and 1220, respectively showing results of a linear regression, chi-squared and cross-correlation regression model, for the GluFib peptide EGVND-NEEGFFSAR, searched against a small cow library and reduced to the top 30 gene symbols. Table 1210 shows results when the following filters are applied: YYZ_SequentialB>2 AND YYZ_SequentialY>2 AND log (IonMatchIntensityRatio)>2.2 Table 1220 shows results when no filters are applied.

In some embodiments, the peptide identification system 110 can be operated to identify a best matching peptide sequence followed by another round where combinations of the same amino acid sequence plus possible modifications are considered until the most optimal fit is obtained.

At the end, the chance that the observation frequency of the peptide or aptamer sequence is simply a random fit can be directly tested by determining the frequency with which the sequence is obtained from random MS/MS or MSn spectra from computer random or physical noise MS/MS or MSn spectra. The observation frequency may be computed with respect to the total number of MS/MS or MSn spectra collected or generated or by the total number of fits from MS/MS or MSn spectra to real or hypothetical peptide sequences.

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to below as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Various embodiments have been described herein by way of example only. Various modification and variations may be made to these example embodiments without departing from the spirit and scope of the invention, which is limited only by the appended claims.

```
                            SEQUENCE LISTING

Sequence total quantity: 28
SEQ ID NO: 1              moltype = AA  length = 14
FEATURE                  Location/Qualifiers
source                   1..14
                         mol_type = protein
                         organism = Homo sapiens
SEQUENCE: 1
EGVNDNEEGF FSAR                                              14

SEQ ID NO: 2              moltype = AA  length = 8
FEATURE                  Location/Qualifiers
source                   1..8
                         mol_type = protein
                         organism = synthetic construct
SEQUENCE: 2
DXVYIHPF                                                     8

SEQ ID NO: 3              moltype = AA  length = 12
FEATURE                  Location/Qualifiers
source                   1..12
                         mol_type = protein
                         organism = synthetic construct
SEQUENCE: 3
RDHSNCLFGN LF                                                12

SEQ ID NO: 4              moltype = AA  length = 12
FEATURE                  Location/Qualifiers
source                   1..12
                         mol_type = protein
                         organism = synthetic construct
SEQUENCE: 4
RERSQMAWNI GY                                                12

SEQ ID NO: 5              moltype = AA  length = 12
FEATURE                  Location/Qualifiers
source                   1..12
                         mol_type = protein
                         organism = synthetic construct
SEQUENCE: 5
KEKTQCVFPC VF                                                12

SEQ ID NO: 6              moltype = AA  length = 12
FEATURE                  Location/Qualifiers
source                   1..12
                         mol_type = protein
                         organism = synthetic construct
SEQUENCE: 6
FWGMYSAGQE RK                                                12

SEQ ID NO: 7              moltype = AA  length = 12
FEATURE                  Location/Qualifiers
source                   1..12
                         mol_type = protein
                         organism = synthetic construct
SEQUENCE: 7
XEDXWKXCTF AX                                                12

SEQ ID NO: 8              moltype = AA  length = 8
FEATURE                  Location/Qualifiers
source                   1..8
                         mol_type = protein
                         organism = synthetic construct
SEQUENCE: 8
DRYVHPIF                                                     8

SEQ ID NO: 9              moltype = AA  length = 8
FEATURE                  Location/Qualifiers
```

-continued

```
source                  1..8
                        mol_type = protein
                        organism = synthetic construct
SEQUENCE: 9
DRPHIFYV                                                                  8

SEQ ID NO: 10           moltype = AA  length = 8
FEATURE                 Location/Qualifiers
source                  1..8
                        mol_type = protein
                        organism = synthetic construct
SEQUENCE: 10
DVYHIRPF                                                                  8

SEQ ID NO: 11           moltype =   length =
SEQUENCE: 11
000

SEQ ID NO: 12           moltype = AA  length = 8
FEATURE                 Location/Qualifiers
source                  1..8
                        mol_type = protein
                        organism = synthetic construct
SEQUENCE: 12
IVHYDFRP                                                                  8

SEQ ID NO: 13           moltype = AA  length = 8
FEATURE                 Location/Qualifiers
source                  1..8
                        mol_type = protein
                        organism = synthetic construct
SEQUENCE: 13
FHIDYVRP                                                                  8

SEQ ID NO: 14           moltype = AA  length = 8
FEATURE                 Location/Qualifiers
source                  1..8
                        mol_type = protein
                        organism = synthetic construct
SEQUENCE: 14
DRIYPVHF                                                                  8

SEQ ID NO: 15           moltype = AA  length = 15
FEATURE                 Location/Qualifiers
source                  1..15
                        mol_type = protein
                        organism = Bos taurus
SEQUENCE: 15
EYGLPAVVGV EHATK                                                         15

SEQ ID NO: 16           moltype = AA  length = 6
FEATURE                 Location/Qualifiers
source                  1..6
                        mol_type = protein
                        organism = Bos taurus
SEQUENCE: 16
TLYYAR                                                                    6

SEQ ID NO: 17           moltype = AA  length = 16
FEATURE                 Location/Qualifiers
source                  1..16
                        mol_type = protein
                        organism = Bos taurus
SEQUENCE: 17
GAIVAIMTQP SANDGK                                                        16

SEQ ID NO: 18           moltype = AA  length = 16
FEATURE                 Location/Qualifiers
source                  1..16
                        mol_type = protein
                        organism = Bos taurus
SEQUENCE: 18
ADVQGSVEAL AAALQK                                                        16

SEQ ID NO: 19           moltype = AA  length = 16
FEATURE                 Location/Qualifiers
source                  1..16
                        mol_type = protein
                        organism = Bos taurus
```

-continued

```
SEQUENCE: 19
ADISIPIMVG GAALSR                                                    16

SEQ ID NO: 20            moltype = AA   length = 7
FEATURE                  Location/Qualifiers
source                   1..7
                         mol_type = protein
                         organism = Bos taurus
SEQUENCE: 20
ALQIVSR                                                              7

SEQ ID NO: 21            moltype = AA   length = 14
FEATURE                  Location/Qualifiers
source                   1..14
                         mol_type = protein
                         organism = Bos taurus
SEQUENCE: 21
GAPAIMKPFE EILR                                                     14

SEQ ID NO: 22            moltype = AA   length = 21
FEATURE                  Location/Qualifiers
source                   1..21
                         mol_type = protein
                         organism = Bos taurus
SEQUENCE: 22
HTAPHVTLMD EVDVTNLVAH R                                             21

SEQ ID NO: 23            moltype = AA   length = 22
FEATURE                  Location/Qualifiers
source                   1..22
                         mol_type = protein
                         organism = Bos taurus
SEQUENCE: 23
IQVIMVGDED QLPSVGPGQV LR                                            22

SEQ ID NO: 24            moltype = AA   length = 22
FEATURE                  Location/Qualifiers
source                   1..22
                         mol_type = protein
                         organism = Bos taurus
SEQUENCE: 24
SVDDYQECYL AMPVPSHAVV AR                                            22

SEQ ID NO: 25            moltype = AA   length = 8
FEATURE                  Location/Qualifiers
source                   1..8
                         mol_type = protein
                         organism = synthetic construct
SEQUENCE: 25
DFVYIHPF                                                             8

SEQ ID NO: 26            moltype = AA   length = 8
FEATURE                  Location/Qualifiers
source                   1..8
                         mol_type = protein
                         organism = Homo sapiens
SEQUENCE: 26
DRVYIHPF                                                             8

SEQ ID NO: 27            moltype = AA   length = 8
FEATURE                  Location/Qualifiers
source                   1..8
                         mol_type = protein
                         organism = synthetic construct
SEQUENCE: 27
DUVYIHPF                                                             8

SEQ ID NO: 28            moltype = AA   length = 8
FEATURE                  Location/Qualifiers
source                   1..8
                         mol_type = protein
                         organism = synthetic construct
SEQUENCE: 28
DYVYIHPF                                                             8
```

The invention claimed is:

1. A method for identifying a peptide for a query spectrum, the method comprising:

generating the query spectrum with a mass spectrometer;

receiving one or more parameters of the query spectrum;

generating one or more candidate peptide sequences based on the one or more parameters of the query spectrum;

generating a plurality of samples of the query spectrum;

selecting at least one sample from the plurality of samples for comparison with the one or more candidate peptide sequences;

determining a likelihood indicator for each of the one or more candidate peptide sequences based on a comparison with the at least one sample;

applying a signal to noise filter to the one or more candidate peptide sequences, wherein the signal to noise filter comprises:

(i) determining an observation frequency of each candidate peptide sequence in real data;

(ii) determining an expected observation frequency of each candidate peptide sequence in noise or random MS/MS spectra; and (iii) applying a Chi Square test to compare the observation frequency in the real data to the expected frequency in noise or random spectra, and filtering the candidate peptide sequences based on the result of the Chi Square test; wherein the candidate peptide sequences are selected from a library of known peptide sequences; and selecting at least one candidate peptide sequence as a proposed peptide sequence for the query spectrum based on the filtered candidate peptide sequences.

2. The method of claim 1, wherein selecting at least one sample from the plurality of samples for comparison with the one or more candidate peptide sequences comprises, for each sample:

counting a number of matching sequential b and y spectra lines of that sample; and if the number of matching sequential b and y spectra lines of that sample is less than a pre-determined minimum number of spectra lines, excluding that sample from comparison with the one or more candidate peptide sequences.

3. The method of claim 1, wherein selecting at least one sample from the plurality of samples for comparison with the one or more candidate peptide sequences comprises, for each sample:

determining a spectra intensity of that sample;

determine a number of matching b and y spectra lines;

for the matching b and y spectra lines, determining a corresponding sum of the spectra intensity;

determining a total sum of the spectra intensity;

determining a ratio of the sum of the spectra intensity for the matching b and y spectra lines and the total sum of the spectra intensity; and if the ratio is less than a pre-determined threshold, excluding that sample from comparison with the one or more candidate peptide sequences.

4. The method of claim 1, wherein selecting at least one sample from the plurality of samples for comparison with the one or more candidate peptide sequences comprises, for each sample:

determining a precursor mass for that sample; and if the precursor mass is substantially equal to a mass of a candidate peptide sequence, selecting that sample for comparison with the one or more candidate peptide sequences.

5. The method of claim 4, wherein the precursor mass comprises at least one of a precursor mass at a charge state of 1, 2, or 3 and wherein the precursor mass comprises a mass shift from one or more post-translational modifications.

6. The method of claim 1, wherein selecting at least one sample from the plurality of samples for comparison with the one or more candidate peptide sequences comprises, for each sample:

determining a mass of a theoretical ion of the sample; and if the mass of the theoretical ion is substantially equal to a mass of a base peak, selecting that sample for comparison with the one or more candidate peptide sequences.

7. The method of claim 1, wherein determining a likelihood indicator for each of the one or more candidate peptide sequences based on a comparison with the at least one sample comprises one or more of:

using one or more of linear regression, multiple linear regression, nested regression or linear model;

using a chi square test to compare theoretical ions of that sample with corresponding theoretical ions of the candidate peptide sequence; and determining a cross correlation score relative to the candidate peptide sequence.

8. The method of claim 1, wherein applying a signal to noise filter to the one or more candidate peptide sequences comprises:

generating random source noise spectra at high frequencies;

determining a difference between the random source noise spectra at high frequencies to the one or more candidate peptide sequences; and if the difference does not exceeds a pre-determined threshold difference, excluding the sample from selection as a proposed peptide sequence for the query spectrum;

otherwise including that sample for selection as a proposed peptide sequence.

9. The method of claim 1, wherein generating one or more candidate peptide sequences based on the one or more parameters of the peptide query comprises one or more of:

storing a plurality of peptide sequences in a computer-readable medium;

selecting, from the computer-readable medium, at least one of the plurality of stored peptide sequences to use as at least one candidate peptide sequence, based on the one or more parameters; and randomly generating at least one candidate peptide sequence, based on the one or more parameters.

10. The method of claim 9, wherein:

receiving one or more parameters of the query spectrum comprises receiving the one or more parameters from user input at a computing device; and the one or more parameters comprise one or more of an amino acid, a position of the amino acid, an amino acid group, a position of the amino acid group, a neutral loss, a post-translational modification shift, an immonium ion, a subtraction of a B ion, or a subtraction of a Y ion.

11. The method of claim 9, wherein selecting, from the computer-readable medium, at least one of the plurality of stored peptide sequences to use as at least one candidate peptide sequence, based on the one or more parameters comprises:

identifying a subset of peptide sequences from the plurality of stored peptide sequences, wherein the plurality of stored peptide sequences comprises one or more of: a naturally occurring peptide sequence and a synthetic peptide sequence, each peptide sequence satisfying the one or more parameters; and selecting the at least one candidate peptide sequence from the subset of peptide sequences.

12. The method of claim 9, wherein randomly generating at least one candidate peptide sequence, based on the one or more parameters comprises:

randomly generating a peptide sequence;

determining whether the randomly generated peptide sequence satisfies the one or more parameters; and if the randomly generated peptide sequence satisfies the one or more parameters, use the randomly generated peptide sequence as a candidate peptide sequence, otherwise discard the randomly generated peptide sequence.

13. The method of claim 12, wherein randomly generating at least one candidate peptide sequence, based on the one or more parameters comprises, for each randomly generated candidate peptide sequence:

assigning at least one amino acid to the randomly generated candidate peptide sequence based on the one or more parameters;

randomly selecting an unassigned position of the pre-determined length;

for the unassigned position:

randomly selecting an amino acid; and assigning the amino acid to the unassigned position; and continue randomly assigning amino acids to the randomly generated candidate peptide sequence until each position is assigned.

14. The method of claim 13, wherein randomly selecting an amino acid comprises:

randomly selecting an amino acid group from a plurality of amino acid groups, each amino acid group comprising a plurality of amino acids; and randomly selecting the amino acid from the randomly selected amino acid group.

15. The method of claim 14, wherein each randomly generated candidate peptide sequence comprises at least one amino acid from each amino acid group of the plurality of amino acid groups.

16. The method of claim 15, wherein generating a plurality of samples of the query spectrum comprises one or more of generating experimental spectra or generating simulated spectra, and generating simulated spectra comprises using a Monte Carlo random simulation.

17. A system for identifying a peptide for a query spectrum, the system comprising a non-transitory computer readable medium and a processor, the processor operable to:

generate the query spectrum with a mass spectrometer;

receive one or more parameters of a query spectrum;

generate one or more candidate peptide sequences based on the one or more parameters of the query spectrum;

generate a plurality of samples of the query spectrum;

select at least one sample from the plurality of samples for comparison with the one or more candidate peptide sequences;

determine a likelihood indicator for each of the one or more candidate peptide sequences based on a comparison with the at least one sample;

apply a signal to noise filter to the one or more candidate peptide sequences, wherein the signal to noise filter is configured to:

(i) determine an observation frequency of each candidate peptide sequence in real data;

(ii) determine an expected observation frequency of each candidate peptide sequence in noise or random MS/MS spectra; and (iii) apply a Chi Square test to compare the observation frequency in the real data to the expected frequency in noise or random spectra, and filter the candidate peptide sequences based on the result of the Chi Square test;

wherein the candidate peptide sequences are selected from a library of known peptide sequences; and select at least one candidate peptide sequence as a proposed peptide sequence for the query spectrum based on the filtered candidate peptide sequences.

18. The system of claim 17, wherein the processor is operable to, for each sample:

count a number of matching sequential b and y spectra lines of that sample; and if the number of matching sequential b and y spectra lines of that sample is less than a pre-determined minimum number of spectra lines, exclude that sample from comparison with the one or more candidate peptide sequences.

19. The system of claim 18, wherein the processor is operable to, for each sample:

determine a spectra intensity of that sample;

for the matching sequential b and y spectra lines, determine a corresponding sum of the spectra intensity;

determine a total sum of the spectra intensity;

determine a ratio of the sum of the spectra intensity for the matching sequential b and y spectra lines and the total sum of the spectra intensity; and if the ratio is less than a pre-determined threshold, exclude that sample from comparison with the one or more candidate peptide sequences.

20. The system of claim 17, wherein the processor is operable to, for each sample:

determine a precursor mass for that sample; and if the precursor mass is substantially equal to a mass of a candidate peptide sequence, select that sample for comparison with the one or more candidate peptide sequences.

21. The system of claim 20, wherein the precursor mass comprises at least one of a precursor mass at a charge state of 1, 2, or 3, and wherein the precursor mass comprises a mass shift from one or more post-translational modifications.

22. The system of claim 17, wherein the processor is operable to, for each sample:

determine a mass of a theoretical ion of the sample; and if the mass of the theoretical ion is substantially equal to a mass of a base peak, select that sample for comparison with the one or more candidate peptide sequences.

23. The system of claim 17, wherein the processor is operable to, for each sample, use one or more of:

linear regression, multiple linear regression, or nested regression;

a chi square test to compare theoretical ions of that sample with corresponding theoretical ions of the candidate peptide sequence; and a cross correlation score relative to the candidate peptide sequence, to determine a likelihood indicator for that sample based on a comparison with the one or more candidate peptide sequences.

24. The system of claim 17, wherein the processor is operable to:

generate random source noise spectra at high frequencies;

determine a difference between the random source noise spectra at high frequencies to the one or more candidate peptide sequences; and if the difference does not exceed a pre-determined threshold difference, exclude the sample from selection as a proposed peptide sequence for the query spectrum;

otherwise include that sample for selection as a proposed peptide sequence.

25. The system of claim 17, wherein the processor is operable to:

store a plurality of peptide sequences in a computer-readable medium;

select, from the computer-readable medium, at least one of the plurality of stored peptide sequences to use as at least one candidate peptide sequence of the one or more candidate peptide sequences, based on the one or more parameters; and randomly generate at least one candidate peptide sequence of the one or more candidate peptide sequences, based on the one or more parameters.

26. The system of claim 25, wherein the processor is operable to:

receive the one or more parameters from user input at a computing device, the one or more parameters comprise one or more of an amino acid, a position of the amino acid, an amino acid group, a position of the amino acid group, a neutral loss, a post-translational modification shift, an immonium ion, a subtraction of a B ion, or a subtraction of a Y ion.

27. The system of claim 25, wherein the processor is operable to:

identify a subset of peptide sequences from the plurality of stored peptide sequences, wherein the plurality of stored peptide sequences comprises one or more of: a naturally occurring peptide sequence and a synthetic peptide sequence, each peptide sequence satisfying the one or more parameters; and select the at least one candidate peptide sequence from the subset of peptide sequences.

28. The system of claim 25, wherein the processor is operable to:

randomly generate a peptide sequence;

determine whether the randomly generated peptide sequence satisfies the one or more parameters; and if the randomly generated peptide sequence satisfies the one or more parameters, use the randomly generated peptide sequence as a candidate peptide sequence, otherwise discard the randomly generated peptide sequence.

29. The system of claim 25, wherein the processor is operable to:

assign at least one amino acid to the randomly generated candidate peptide sequence based on the one or more parameters;

randomly select an unassigned position of the pre-determined length;

for the unassigned position:

randomly select an amino acid; and assign the amino acid to the unassigned position; and continue to randomly assign amino acids to the randomly generated candidate peptide sequence until each position is assigned.

30. The system of claim 29, wherein the processor is operable to:

randomly select an amino acid group from a plurality of amino acid groups, each amino acid group comprising a plurality of amino acids; and randomly select the amino acid from the randomly selected amino acid group.

31. The system of claim 30, wherein each randomly generated candidate peptide sequence comprises at least one amino acid from each amino acid group of the plurality of amino acid group.

32. The system of claim 17, wherein the processor is operable to generate experimental spectra or simulated spectra, and wherein the processor is operable to use a Monte Carlo random simulation to generate simulated spectra.

* * * * *